(12) United States Patent
Manosroi et al.

(10) Patent No.: US 7,087,412 B2
(45) Date of Patent: *Aug. 8, 2006

(54) METHODS FOR LARGE SCALE PROTEIN PRODUCTION IN PROKARYOTES

(75) Inventors: Jiradej Manosroi, Chiang Mai (TH);
Aranya Manosroi, Chiang Mai (TH);
Chatchai Tayapiwatana, BKK (TH);
Friedrich Goetz, Tuebingen (DE);
Rolf-Guenther Werner, Biberach (DE)

(73) Assignee: Boehringer Ingelheim International GmbH (DE)

( * ) Notice: Subject to any disclaimer, the term of this patent is extended or adjusted under 35 U.S.C. 154(b) by 218 days.

This patent is subject to a terminal disclaimer.

(21) Appl. No.: 09/987,457

(22) Filed: Nov. 14, 2001

(65) Prior Publication Data

US 2003/0013150 A1 Jan. 16, 2003

Related U.S. Application Data

(60) Provisional application No. 60/268,573, filed on Feb. 15, 2001.

(30) Foreign Application Priority Data

Nov. 14, 2000 (GB) .......................... 0027782.2

(51) Int. Cl.
*C12P 21/06* (2006.01)
*C12P 21/04* (2006.01)
*C07K 1/00* (2006.01)
*C07K 14/00* (2006.01)

(52) U.S. Cl. ...................... 435/71.1; 435/69.1; 530/350

(58) Field of Classification Search ................ 530/350; 435/69.1, 71.1

See application file for complete search history.

(56) References Cited

U.S. PATENT DOCUMENTS

| 5,840,533 | A | | 11/1998 | Niwa et al. | |
| 6,027,888 | A | * | 2/2000 | Georgiou et al. | ............... 435/6 |
| 6,083,715 | A | | 7/2000 | Georgiou et al. | |
| 2003/0013150 | A1 | | 1/2003 | Manosroi et al. | |
| 2003/0049729 | A1 | * | 3/2003 | Manosroi et al. | .......... 435/69.1 |

FOREIGN PATENT DOCUMENTS

| EP | 0 302 456 A1 | 2/1989 |
| EP | 0 357 391 A2 | 3/1990 |
| EP | 0 467 676 A2 | 1/1992 |
| EP | 1 048 732 A1 | 11/2000 |
| EP | 1 077 263 A1 | 2/2001 |
| WO | WO 97/38123 A1 | 10/1997 |
| WO | WO 98/54199 A1 | 12/1998 |
| WO | WO 02/40650 | 5/2002 |
| WO | WO 02/40696 | 5/2002 |

OTHER PUBLICATIONS

Sivaprasadarao et al. Expression of funcitonal human retinol–binding protein in *Escheria coli* using a secretion vector Biochemical Journal vol. 296 Pt. 1 1993 pp. 209–215.*
Accession No. E02814 (Habuka et al. JP1991076580).*
Allen, S. et al., "Intracellular Folding of Tissue–type Plasminogen Activator. Effects of Disulfide Bond Formation on N–Linked Glycosylation and Secretion," *J. Biol. Chem.* 270:4797–4804, The American Society for Biochemistry and Molecular Biology, Inc. (1995).
Ames, G.F.–L. et al., "Simple, Rapid, and Quantitative Release of Periplasmic Proteins by Chloroform," *J. Bacteriol.* 160:1181–1183, American Society for Microbiology (1984).
Barbas, C.F. III et al., "Assembly of combinatorial antibody libraries on phage surfaces: The gene III site," *Proc. Natl. Acad. Sci. U.S.A.* 88:7978–7982, The National Academy of Sciences of the U.S.A. (1991).
Barbas, C.F. III and J. Wagner, "Synthetic Human Antibodies: Selecting and Evolving Functional Proteins," *Methods* 8:94–103, Academic Press (1995).
Bennett, W.F. et al., "High Resolution Analysis of Functional Determinants on Human Tissue–type Plasminogen Activator," *J. Biol. Chem.* 266: 5191–5201, The American Society for Biochemistry and Molecular Biology, Inc. (1991).
Betton, J.–M. et al., "Degradation *versus* Aggregation of Misfolded Maltose–binding Protein in the Periplasm of *Escherichia coli*," *J. Biol. Chem.* 273:8897–8902, The American Society for Biochemistry and Molecular Biology, Inc. (1998).
Camiolo, S.M. et al., "Fibrinogenolysis and Fibrinolysis with Tissue Plasminogen Activator, Urokinase, Streptokinase–Activated Human Globulin and Plasmin," *Proc. Soc. Exp. Biol. Med.* 138:277–280, Academic Press (1971).
Cartwright, T., "Production of tPA from Animal Cell Cultures," In *Animal Cell Biotechnology*, vol. 5, R.E. Spier and J.B. Griffiths (eds.), Academic Press, N.Y. p. 217–245 (1992).
Curry, K.A. et al., "*Escherichia coli* Expression and Processing of Human Interleukin–1β Fused to Signal Peptides," *DNA Cell Biol.* 9:167–175, Mary Ann Liebert, Inc. (1990).

(Continued)

*Primary Examiner*—James Ketter
*Assistant Examiner*—Konstantina Katcheves
(74) *Attorney, Agent, or Firm*—Sterne, Kessler, Goldstein & Fox, P.L.L.C.

(57) ABSTRACT

The invention belongs to the field of protein production in prokaryotic cells. The invention relates to methods for the production of recombinant DNA-derived heterologous protein in prokaryotic cells, wherein the heterologous protein is secreted extracellularly as an active and correctly folded protein, and the prokaryotic cell contains and expresses a vector comprising the DNA coding for the heterologous protein operably linked to the DNA coding for the signal peptide OmpA.

49 Claims, 16 Drawing Sheets

OTHER PUBLICATIONS

Datar, R.V. et al., "Process Economics of Animal Cell and Bacterial Fermentations: A Case Study Analysis of Tissue Plasminogen Activator," *Bio/Technology* 11:349–357, Nature Publishing Company (1993).

Denèfle, P. et al., "Heterologous protein export in *Escherichia coli*: influence of bacterial signal peptides on the export of human interleukin 1β," *Gene* 85:499–510, Elsevier Science Publishers B.V. (Biomedical Division) (1989).

Griffiths, J.B. and A. Electricwala, "Production of Tissue Plasminogen Activators from Animal Cells," *Adv. Biochem. Eng. Biotechnicol.* 34:147–166, Springer–Verlag (1987).

Harris, T.J.R. et al., "Cloning of cDNA Coding for Human Tissue–type Plasminogen Activator and its Expression in *Escherichia coli*," *Mol. Biol. Med.* 3:279–292, Academic Press Inc. (1986).

Heussen, C. and E.B. Dowdle, "Electrophoretic Analysis of Plasminogen Activators in Polyacrylamide Gels Containing Sodium Dodecyl Sulfate and Copolymerized Substrates," *Anal. Biochem.* 102:196–202, Academic Press, Inc. (1980).

Heussen, C. et al., "Purification of Human Tissue Plasminogen Activator with *Erythrina* Trypsin Inhibitor," *J. Biol. Chem.* 259:11635–11638, The American Society of Biological Chemists, Inc. (1984).

Hu, C.–K. et al., "Tissue–Type Plasminogen Activator Domain–Deletion Mutant BM 06.022: Modular Stability, Inhibitor Binding, and Activation Cleavage," *Biochemistry* 33:11760–11766, American Chemical Society (1994).

Kipriyanov, S.M. et al., "High level production of soluble single chain antibodies in small–scale *Escherichia coli* cultures," *J. Immunol. Methods* 200:69–77, Elsevier Science B.V. (1997).

Ko, J.H. et al., "High–level Expression and Secretion of Streptokinase in *Escherichia coli*," *Biotechnol. Lett.* 17:1019–1024, Chapman & Hall (1995).

Kouzuma, Y. et al., "The Tissue–Type Plasminogen Activator Inhibitor ETIa from *Erythrina variegata*: Structural Basis for the Inhibitory Activity by Cloning, Expression, and Mutagenesis of the cDNA Encoding ETIa," *J. Biochem. (Tokyo)* 121:456–463, The Japanese Biochemical Society (1997).

Lasters, I. et al., "Enzymatic properties of phage–displayed fragments of human plasminogen," *Eur. J. Biochem.* 244:946–952, Springer International on behalf of the Federation of European Biochemical Societies (1997).

Lobel, L.I. et al., "Filamentous Phage Displaying the Extracellular Domain of the hLH/CG Receptor Bind hCG Specifically," *Endocrinology* 138:1232–1239. The Endocrine Society (1997).

Lubiniecki, A. et al., "Selected Strategies for Manufacture and Control of Recombinant Tissue Plasminogen Activator Prepared from Cell Cultures," In *Advances In Animal Cell Biology and Technology for Bioprocesses*, R.E. Spier et al., (ed.), Butterworth & Co., London, p. 442–451 (1989).

Lucic, M.R. et al., "Secretion in *Escherichia coli* and phage–display of recombinant insulin–like growth factor binding protein–2," *J. Biotechnical.* 61:95–108, Elsevier Science B.V. (1998).

Martin, U. et al., "Properties of a novel plasminogen activator (BM 06.022) produced in *Escherichia coli*," *Z. Kardiol.* 79:167–170, Steinkopff Verlag Darmstadt (1990).

Obukowicz, M.G. et al., "Secretion of Active Kringle–2–Serine Protease in *Escherichia coli*," *Biochemistry* 29:9737–9745, American Chemical Society (1990).

Parmley, S.F. and G.P. Smith, "Antibody–selectable filamentous fd phage vectors: affinity purification of target genes," *Gene* 73:305–318, Elsevier Science Publishers B.V. (1988).

Pennica, D. et al., "Cloning and expression of human tissue–type plasminogen activator cDNA in *E. coli*," *Nature* 301:214–221, Macmillan Journals Ltd. (1983).

Rippmann, J.F. et al., "Procaryotic Expression of Single–Chain Variable–Fragment (scFv) Antibodies: Secretion in L–Form Cells of *Proteus mirabilis* Leads to Active Product and Overcomes the Limitations of Periplasmic Expression in *Escherichia coli*," *Appl. Environ. Microbiol.* 64:4862–4869, American Society for Microbiology (1998).

Saito, Y. et al., "Production and Characterization of a Novel Tissue–Type Plasminogen Activator Derivative in *Escherichia coli*," *Biotechnol. Prog.* 10:472–479, American Chemical Society and American Institute of Chemical Engineers (1994).

Sarmientos, P. et al., "Synthesis and Purification of Active Human Tissue Plasminogen Activator from *Escherichia coli*," *Bio/Technology* 7:495–501, Nature Publishing Company (1989).

Scherrer, S. et al., "Periplasmic aggregation limits the proteolytic maturization of the *Escherichia coli* Penicillin G amidase precursor polypeptide," *Appl. Microbiol. Biotechnol.* 42:85–91, Springer–Verlag (1994).

Soeda, S. et al., "Rapid and High–Yield Purification of Porcine Heart Tissue–Type Plasminogen Activator by Heparin–Sepharose Choromatography," *Life Sci.* 39:1317–1324, Pergamon Journals Ltd. (1986).

Szarka, S.J. et al., "Staphylokinase as a Plasminogen Activator Component in Recombinant Fusion Proteins," *Appl. Environ. Microbiol.* 65:506–513, American Society for Microbiology (Feb. 1999).

Waldenström, M. et al., "Synthesis and secretion of a fibrinolytically active tissue–type plasminogen activator variant in *Escherichia coli*," *Gene* 99:243–248 (1991).

Wan, E.W.–M., "TolAIII Co–overexpression Facilitates the Recovery of Periplasmic Recombinant Proteins into the Growth Medium of *Escherichia coli*," *Protein Expr. Purif.* 14:13–22, Academic Press (1998).

Zacharias, U. et al., "Characterization of Human Tissue–type Plasminogen Activator with Monoclonal Antibodies: Mapping of Epitopes and Binding Sites for Fibrin and Lysine," *Thromb. Haemost.* 67:88–94, F.K. Schattauer Verlagsgesellschaft mbH (1992).

Andris–Widhopf, J., et al., "Methods for the generation of chicken monoclonal antibody fragments by phage display," *J. Immunol. Meth.* 242:159–181, Elsevier Science B.V. (Aug. 2000).

Hu , S.–z, et al., "Minibody: A Novel Engineered Anti–Carcinoembryonic Antigen Antibody Fragment (Single–Chain Fv–$C_H$3) Which Exhibits Rapid, High–Level Targeting of Xenografts," *Cancer Res.* 56:3055–3061, American Association for Cancer Research (1996).

Huston, J.S., et al., "Protein engineering of antibody binding sites: Recovery of specific activity in an anti–digoxin single–chain Fv analogue produced in *Escherichia coli*," *Proc. Natl. Acad. Sci. USA* 85:5879–5883, National Academy of Science (1988).

Kortt, A.A., et al., "Single–chain Fv fragments of anti–neuraminidase antibody NC10 containing five– and ten–residue linkers form dimers and with zero–residue linker a trimer," *Protein Eng. 10*:423–433, Oxford University Press (1997).

Lovejoy, B., et al., "Crystal Structure of a Synthetic Triple–Stranded α–Helical Bundle," *Science 259*:1288–1293, American Association for the Advancement of Science (1993).

Manosroi, J., et al., "Secretion of Active Recombinant Human Tissue Plasminogen Activator Derivatives in *Escherichia coli*," *Appl. Env. Microbiol. 67*:2657–2664, American Society for Microbiology (Jun. 2001).

NCBI Entrez, Genbank report, Accession No. AF268281, from Rader, C., and Barbas, C.F. III (Oct. 2000).

Pack, P., et al., "Improved Bivalent Miniantibodies, with Identical Avidity as Whole Antiboides, Produced by High Cell Density Fermentation of *Escherichia coli*," *Bio/Technology 11*:1271–1277, Nature Publishing Co. (1993).

Pack, P., et al., "Tetravalent Miniantibodies with High Avidity Assembling in *Escherichia coli*," *J. Mol. Biol. 246*:28–34, Academic Press Ltd. (1995).

Pennica, D., et al., "Cloning and expression of human tissue–type plasminogen activator cDNA in *E. Coli*," *Nature 301*:214–221, Macmillan Journals Ltd. (1983).

Perisic, O., et al., "Crystal structure of a diabody, a bivalent antibody fragment," *Structure 2*:1217–1226, Current Biology Ltd. (1994).

Weiner, M.P., and G.L. Costa, "Rapid PCR Site–directed Mutagenesis," *PCR Meth. Appl. 4*:S131–S136, Cold Spring Harbor Laboratory Pres (1994).

Weiner, M.P., et al., "Site–directed mutagenesis of double–stranded DNA by the polymerase chain reaction," *Gene 151*:119–123, Elsevier Science B.V. (1994).

Dialog File 351, Accession No. 13502244, Derwent WPI English language abstract for EP 1 048 732 A1 (Document AN1).

International Search Report for International Patent Application No. PCT/EP01/12920, mailed Jun. 11, 2002.

Pending U.S. Appl. No. 09/987,455, Manosroi et al., filed Nov. 14, 2001.

Cleary, S., et al., "Purification and Characterization of Tissue Plasminogen Activator Kringle–2 Domain Expressed in *Escherichia coli*," *Biochem. 28*:1884–1891, American Chemical Society (1989).

Qiu, J., et al., "Expression of Active Human Tissue–Type Plasminogen Activator in *Escherichia coli*," *Appl. Environ. Microbiol. 64*:4891–4896, American Society for Microbiology (1998).

Zi–Chun, W., et al., "Synthesis and Expression of a Gene From Kringle–2 Domain of Tissue Plasminogen Activator in *E. Coli*," *Sci. China B. 37*:667–676, Chinese Academy of Sciences (1994).

Dialog File 351, Accession No. 2001–204356/ 200121, Derwent WPI English Language abstract for European Patent Application No. 1 077 263 A1 (Document AM2).

International Search Report for International Patent Application No. PCT/EP01/12857, mailed May 10, 2002.

\* cited by examiner

METHODS FOR LARGE SCALE PROTEIN PRODUCTION IN PROKARYOTES

CROSS-REFERENCE TO RELATED APPLICATIONS

The present application claims priority benefit to Great Britain patent application GB 00 27 782.2, filed Nov. 14, 2000 and to U.S. Provisional Patent Application No. 60/268,573, filed Feb. 15, 2001. The full disclosure of each of these applications is herein incorporated by reference.

BACKGROUND OF THE INVENTION

1. Field of the Invention

The invention belongs to the field of protein production in prokaryotic cells.

The invention relates to methods for the production of recombinant DNA-derived heterologous protein in prokaryotic cells, wherein said heterologous protein is secreted extracellularly as an active and correctly folded protein, and the prokaryotic cell contains and expresses a vector comprising the DNA coding for said heterologous protein operably linked to the DNA coding for the signal peptide OmpA.

2. Related Art

Prokaryotic expression systems for heterologous proteins are commonly used for proteins which do not require mammalian glycosylation patterns as they provide a cheap way of producing large quantities of said protein. The formation of highly aggregated protein or inclusion bodies can be commonly found in high-level expression of many heterologous proteins in E. coli. One way of protein production is via inclusion bodies which develop in cytoplasm. Cell wall and outer membrane components of the prokaryotic cells used for production (e.g. E. coli) usually contaminate the cell lysate containing the heterologous protein when said inclusion bodies are prepared by low-speed centrifugation. The outer membrane component can be eliminated by selective extraction with detergents and low concentrations of either urea or guanidine.HCl.

One example of such a heterologous protein is a tPA derivative. Tissue plasminogen activator (tPA) is a polypeptide containing 527 amino acid residues (Pennica, D., et al., Nature 301:214–221 (1983)) with a molecular mass of 72 kDa. The molecule is divided into five structural domains. Nearby the N-terminal region is a looped finger domain, which is followed by a growth factor domain. Two similar domains, kringle 1 and kringle 2, are following. Both finger and kringle 2 domains bind specifically to the fibrin clots thereby accelerating tPA protein activation of bound plasminogen. Downstream of kringle 2 is the serine protease, with its catalytic site located at the C-terminus. The serine protease is responsible for converting plasminogen to plasmin a reaction important in the homeostasis of fibrin formation and clot dissolution. The correct folding of tPA requires the correct pairing of 17 disulfide bridges in the molecule (Allen, S., et al., J. Biol. Chem. 270:4797–4804 (1995)).

Clinically, tPA is a thrombolytic agent of choice for the treatment of acute myocardial infarction. It has the advantage of causing no side effects on systemic haemorrhaging and fibrinogen depletion (Camiolo, S. M., et al., Proc. Soc. Exp. Biol. Med. 38:277–280 (1971)). Bowes melanoma cells were first used as a source in tPA production for therapeutic purposes (Griffiths, J. B., and Electricwala, A., Adv. Biochem. Eng. Biotechnol. 34:147–166 (1987)). Since a consistent process with efficient production of highly purified protein in good yield is required for clinical use, the construction of full-length recombinant-tPA (r-tPA) progressed to mammalian cells. Chinese hamster ovary cells were transfected with the tPA gene to synthesize the r-tPA (Cartwright, T., "Production of t-PA from animal cell culture," in Spier, R. E. and Griffiths, J. B., eds., Animal Cell Biotechnology, Vol. 5., Academic Press, New York (1992), pp. 217–245; Lubiniecki, A., et al., "Selected strategies for manufacture and control of recombinant tissue plasminogen activator prepared from cell culture," in Spier, R. E., et al., eds., Advances in animal cell biology and technology for bioprocesses, Butterworths, London (pp. 442–451). The recombinant product produced by a mammalian fermentation system was harvested from the culture medium. Attracted by simplicity and economy of production, a number of efforts in producing r-tPA from bacteria, especially from Escherichia coli, were investigated (Datar, R. V., et al., Biotechnology 11:349–357 (1993); Harris, T. J., et al., Mol. Biol. Med. 3:279–292 (1986); Sarmientos, P., et al., Biotechnology 7:495–501 (1989)). Regarding the low yield and the formation of inclusion bodies, which resulted in misfolding and in an inactive enzyme, numerous strategies have been proposed to overcome these problems. The major criterion is to synthesize the smallest molecule, which is still active instead of full-length tPA.

Several deletion-mutant variants including kringle 2 plus serine protease (K2S) were considered. However, the enzymatic activity of the recombinant-K2S (r-K2S) was obtained only when refolding processes of purified inclusion bodies from cytoplasmic compartment were achieved (Hu, C. K., et al., Biochemistry 33:11760–11766 (1994); Saito, Y., et al., Biotechnol. Prog. 10:472–479 (1994)). In order to avoid the cumbersome refolding processes and periplasmic protein delivery, special bacterial expression systems were exploited (Betton, J. M., et al., J. Biol. Chem. 273:8897–8902 (1998); Scherrer, S., et al., Appl. Microbiol. Biotechnol. 42:85–89 (1994)). Despite periplasmic expression of tPA, overexpression led to inactive aggregates, even in the relatively high oxidizing condition in the periplasm.

In the prior art, there are a few descriptions of methods for the preparation of recombinant K2S in E. coli. However, there is no disclosure of a method leading to a cost effective method for large scale production of biologically active K2S.

Obukowicz, M. G., et al., Biochemistry 29:9737–9745 (1990), expressed and purified r-K2S from periplasmic space. The obvious disadvantage of this method was an extra periplasmic extraction step, which is not suitable for large scale production.

Saito, Y., et al., Biotechnol. Prog. 10:472–479 (1994), disclose the cytoplasmic expression of r-K2S. The authors used an in vivo renaturation processes for the expressed r-K2S, which was purified from the cytoplasmic space of E. coli as inclusion body. Boehringer Mannheim use a similar cumbersome denaturing/refolding process involving the steps of cell digestion, solubilization under denaturing and reducing conditions and reactivation under oxidizing conditions in the presence of GSH/GSSG which is not cost effective and requires mutation of the amino acid sequence (Martin, U., et al., Z. Kardiol. 79:167–170 (1990)).

In 1991, Waldenström, M., et al., Gene 99:243–248 (1991), constructed a vector (pEZZK2P) for the secretion of kringle 2 plus serine protease domain to E. coli culture supernatant. Hydroxylamine was used to remove the ZZ fusion peptide from IgG-Sepharose purified fraction. The cleavage agent hydroxylamine required modification of the cleavage sites of kringle 2 plus serine protease (Asn[177]→Ser and Asn[184]→Gln) thus to protect it from hydroxylamine digestion. However, the resulting non-native, not properly folded K2S molecule is not suitable for therapeutic purposes. The unusual sequence may even activate the human immune system.

SUMMARY OF THE INVENTION

The problem underlying the present invention was thus to provide a commercially applicable method for large scale production of heterologous proteins, e.g. K2S, wherein the heterologous protein is secreted in its biologically active form into the culture supernatant.

The problem was solved within the scope of the claims and specification of the present invention.

DETAILED DESCRIPTION OF THE PREFERRED EMBODIMENTS

Figure 1:
FIG. 1. Validation of PCR amplification product of the K2S gene from the p51-3 vector by using sK2/174 and ASSP primers. Lane 1 shows 1 kb marker (Roche Molecular Biochemicals, Indianapolis, Ind.). Lane 2 was loaded with 1 μl of amplified product. A single band at 1110 bp is depicted. The electrophoresis was performed on a 1% agarose gel.

The use of the singular or plural in the claims or specification is in no way intended to be limiting and also includes the other form.

The invention relates to a method for the production of recombinant DNA-derived heterologous protein in prokaryotic cells, wherein said heterologous protein is secreted extracellularly as an active and correctly folded protein, characterized in that the prokaryotic cell contains and expresses a vector comprising the DNA coding for said heterologous protein operably linked to the DNA coding for the signal peptide OmpA or a functional derivative thereof.

Surprisingly, the use of the signal peptide OmpA alone and/or in combination with the N-terminal amino acids SEGN/SEGNSD (SEQ ID NO:2/SEQ ID NO:3) translocate the recombinant DNA-derived proteins to the outer surface and facilitates the release of the functional and active molecule into the culture medium to a greater extent than any other method in the prior art. Before crossing the outer membrane, the recombinant DNA-derived protein is correctly folded according to the method of the present invention. The signal peptide is cleaved off to produce a mature molecule. Surprisingly, the efficiency of signal peptide removal is very high and leads to correct folding of the recombinant DNA-derived protein. This method according to the invention, exemplified for the kringle 2 plus serine protease domain (K2S) of tissue plasminogen activator protein in example 1 is generally applicable to expression of several different proteins and polypeptides which do not require mammalian glycosylation in prokaryotic host cells.

The method according to the invention has advantages over methods known in the art- not only that it is a cheap production method due to the prokaryotic host cell used, surprisingly, a correctly folded molecule is secreted to the supernatant.

The skilled person can easily obtain the DNA sequence of a protein of interest to be expressed by the method according to the invention from suitable databases and clone it to be used in the method according to the invention.

Said signal peptide OmpA interacts with SecE and is delivered across the inner membrane by energy generated by SecA, which binds to Sec components (SecE-SecY). SecY forms a secretion pore to dispatch the recombinant DNA-derived protein according to the invention. The space between the outer membrane and inner membrane of Gram-negative bacteria, periplasm, has higher oxidative condition in comparison to the cytoplasmic space. This supports the formation of disulfide bonds and properly folding of the recombinant protein (e.g. K2S) in the periplasm to yield an active molecule. According to the present invention, the signal peptide will be cleaved off to produce a mature molecule. The complex of GspD secretin and GspS lipoprotein on the outer membrane serves as gate channel for secreting the recombinant protein according to the invention to the extracellular medium. This secretion process requires energy, which is generated in cytoplasm by GspE nucleotide-binding protein then transferred to the inner membrane protein (Gsp G-J, F and K-N). GspC transfers the energy to GspD by forming a cross-linker between a set of inner membrane protein (Gsp G-J, F and K-N) and GspD. Before crossing the outer membrane successfully, the recombinant protein is correctly folded.

Operably linked according to the invention means that the DNA encoding the heterologous protein (preferably comprising the nucleic acid encoding SEGN (SEQ ID NO:2) or SEGNSD (SEQ ID NO:3) at its N-terminal portion) is cloned in close proximity to the OmpA DNA into the vector in order to achieve expression of the OmpA-heterologous protein-fusion protein and to direct secretion outside the prokaryotic host cell. Typically, the majority of the heterologous protein is secreted and can then be purified by appropriate methods such as ammonium sulfate precipitation. The invention also includes the use of inducers such as IPTG or IPTG in combination with glycerol, the improvement of the incubation condition and harvesting period to maximize the amount of active protein.

The inventors surprisingly found that the OmpA signal peptide alone or operatively linked to the amino acids characterized by the sequence SEGN (SEQ ID NO:2) or SEGNSD (SEQ ID NO:3) lead to secretion of the heterologous protein into the medium rather than accumulation in the periplasmatic space.

In a preferred embodiment, said DNA encoding the OmpA signal peptide may be fused to a short peptide characterized by the amino acid sequence SEGN (SEQ ID NO:2) or the coding nucleic acid sequence TCTGAGG-GAAAC (SEQ ID NO:4) and located in the N-terminal portion or at the N-terminal portion of the heterologous protein. Thus, preferably, said fusion protein comprises OmpA-SEGN-heterologous protein. Even more preferred, said amino acids characterized by SEGN (SEQ ID NO:2) may be carry a point mutation or may be substituted by a non-natural amino acid. Even more preferred, there may be an amino acid or non-amino acid spacer between OmpA and SEGN (SEQ ID NO:2) or SEGN (SEQ ID NO:2) and the heterologous protein.

In a preferred embodiment, said DNA encoding the OmpA signal peptide may be fused to a short peptide characterized by the amino acid sequence SEGNSD (SEQ ID NO:3) or the coding nucleic acid sequence TCTGAGG-GAAACAGTGAC (SEQ ID NO:5) and located in the N-terminal portion or at the N-terminal portion of the heterologous protein. Thus, preferably, said fusion protein comprises OmpA-SEGNSD-heterologous protein. Even more preferred, said amino acids characterized by SEGNSD (SEQ ID NO:3) may be carry a point mutation or may be substituted by a non-natural amino acid. Even more preferred, there may be an amino acid or non-amino acid spacer between OmpA and SEGNSD (SEQ ID NO:3) or SEGNSD (SEQ ID NO:3) and the heterologous protein.

Thus, in a preferred method according to the invention said the prokaryotic cell contains and expresses a vector comprising the DNA coding for said heterologous protein operably linked to the DNA coding for the signal peptide OmpA which is operably linked to the nucleic acid molecule defined by the sequence TCTGAGGGAAACAGTGAC (SEQ ID NO:5) or a functional derivative thereof.

Such heterologous proteins include, but are not limited to insulin, insulin-like growth factor, hGH, tPA, cytokines, e.g. interleukines (IL) such as IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, interferon (IFN) alpha, IFN beta, IFN gamma, IFN omega or IFN tau, tumor necrosisfactor (TNF) TNF alpha and TNF beta, TRAIL; G-CSF, GM-CSF, M-CSF, MCP-1 and VEGF.

The method according to the invention can be advantageously used for production of antibodies or fragments thereof. Such fragments include e.g. Fab fragments (Fragment antigen-binding=Fab). Fab fragments consist of the variable regions of both chains which are held together by the adjacent constant region. These may be formed by protease digestion, e.g. with papain, from conventional antibodies, but similar Fab fragments may also be produced in the mean time by genetic engineering. Further antibody fragments include F(ab')2 fragments, which may be prepared by proteolytic cleaving with pepsin.

Using genetic engineering methods it is possible to produce shortened antibody fragments which consist only of the variable regions of the heavy (VH) and of the light chain (VL). These are referred to as Fv fragments (Fragment variable=fragment of the variable part). Since these Fv-fragments lack the covalent bonding of the two chains by the cysteines of the constant chains, the Fv fragments are often stabilised. It is advantageous to link the variable regions of the heavy and of the light chain by a short peptide fragment, e.g. of 10 to 30 amino acids, preferably 15 amino acids. In this way a single peptide strand is obtained consisting of VH and VL, linked by a peptide linker. An antibody protein of this kind is known as a single-chain-Fv (scFv). Examples of scFv-antibody proteins of this kind known from the prior art are described in Huston, et al., Proc. Nat. Acad. Sci. 16:5879–5883 (1988).

In recent years, various strategies have been developed for preparing scFv as a multimeric derivative. This is intended to lead, in particular, to recombinant antibodies with improved pharmacokinetic and biodistribution properties as well as with increased binding avidity. In order to achieve multimerisation of the scFv, scFv were prepared as fusion proteins with multimerisation domains. The multimerisation domains may be, e.g. the CH3 region of an IgG or coiled coil structure (helix structures) such as Leucin-zipper domains. However, there are also strategies in which the interaction between the VH/VL regions of the scFv are used for the multimerisation (e.g. dia-, tri- and pentabodies). By diabody the skilled person means a bivalent homodimeric scFv derivative (Hu et al., *Proc. Nat. Acad. Sci.* 16:5879–5883 (1996)). The shortening of the Linker in an scFv molecule to 5–10 amino acids leads to the formation of homodimers in which an inter-chain VH/VL-superimposition takes place. Diabodies may additionally be stabilised by the incorporation of disulphide bridges. Examples of diabody-antibody proteins from the prior art can be found in Perisic, et al., *Structure* 2:1217–1226 (1994).

By minibody the skilled person means a bivalent, homodimeric scFv derivative. It consists of a fusion protein which contains the CH3 region of an immunoglobulin, preferably IgG, most preferably IgG1 as the dimerisation region which is connected to the scFv via a Hinge region (e.g. also from IgG1) and a Linker region. The disulphide bridges in the Hinge region are mostly formed in higher cells and not in prokaryotes. Examples of minibody-antibody proteins from the prior art can be found in Hu et al., *Cancer Res.* 56:3055–3061 (1996).

By triabody the skilled person means a: trivalent homotrimeric scFv derivative (Kortt et al., *Protein Engineering* 10:423–433 (1997). ScFv derivatives wherein VH-VL are fused directly without a linker sequence lead to the formation of trimers.

The skilled person will also be familiar with so-called miniantibodies which have a bi-, tri- or tetravalent structure and are derived from scFv. The multimerisation is carried out by di-, tri- or tetrameric coiled coil structures (Pack et al., *Biotechnology* 11:1271–1277 (1993); Lovejoy et al., *Science* 259:1288–1293 (1993); Pack et al., *J. Mol. Biol.* 246:28–34 (1995)).

Therefore in another preferred method according to the invention an antibody or antibody fragment as described supra is produced.

The method according to the invention comprises prokaryotic host cells such as, but not limited to *Escherichia coli* (*E. coli*), *Bacillus subtilis*, *Streptomyces*, *Pseudomonas*, e.g. *Pseudomonas putida*, *Proteus mirabilis* or *Staphylococcus*, e.g. *Staphylococcus carnosus*. Preferably said host cells according to the invention are Gram-negative bacteria.

Preferably, a method according to the invention is also characterised in that the prokaryotic cell is *E. coli*. Suitable strains include, but are not limited to *E. coli* XL-1 blue, *E. coli* BL21(DE3), *E. coli* JM109, *E. coli* DH series, *E. coli* TOP10 and *E. coli* HB101.

Preferably, a method according to the invention is also characterised in that the following steps are carried out:

a) the DNA encoding the heterologous protein is amplified by PCR;

b) the PCR product is purified;

c) said PCR product is inserted into a vector comprising the DNA coding for OmpA signal peptide and the DNA coding for gpIII in such a way that said PCR product is operably linked upstream to the DNA coding for the OmpA signal sequence and linked downstream to the DNA coding for gpIII of said vector;

d) that a stop codon is inserted between said heterologous protein and gpIII;

e) said vector is expressed by the prokaryotic cell f) the heterologous protein is purified.

For step a) according to the invention the choice/design of the primers is important to clone the DNA in the right location and direction of the expression vector (see example 1). Thus, the primers as exemplified in example 1 and FIG. 4 comprise an important aspect of the present invention. With gp III of step c), gene protein HI is meant which is present mainly in phagemid vectors. The stop codon is inserted to avoid transcription of gp III thus eventually leading to secretion of the heterologous protein of interest. Any suitable method for insertion of the stop codon may be employed such as site-directed mutagenesis (e.g. Weiner, M. P. and Costa, G. L., *PCR Methods Appl.* 4:S131–136 (1994); Weiner, M. P., et al., *Gene* 151:119–123 (1994); see also example 1).

Any vector may be used in the method according to the invention, preferably said vector is a phagemid vector (see below).

The untranslated region may contain a regulatory element, such as e.g. a transcription initiation unit (promoter) or enhancer. Said promoter may, for example, be a constitutive, inducible or development-controlled promoter. Preferably, without ruling out other known promoters, the constitutive promoters of the human Cytomegalovirus (CMV) and Rous sarcoma virus (RSV), as well as the Simian virus 40 (SV40) and Herpes simplex promoter. Inducible promoters according to the invention comprise antibiotic-resistant promoters, heat-shock promoters, hormone-inducible "Mammary tumour virus promoter" and the metallothioneine promoter. Preferred promotors include T3 promotor, T7 promotor, Lac/ara1 and Ltet0-1.

More preferably, a method according to the invention is also characterised in that the DNA encoding the heterologous protein is preceeded by a lac promotor and/or a ribosomal binding site such as the Shine-Dalgarno sequence (see also example).

Suitable vectors according to the invention include, but are not limited to viral vectors such as e.g. Vaccinia, Semliki-Forest-Virus and Adenovirus, phagemid vectors and the like. Preferred are vectors which can be advantageously used in *E. coli*, but also in any other prokaryotic host such as pPROTet.E, pPROLar.A, members of the pBAD family, pSE family, pQE family and pCAL.

Another preferred embodiment of the invention relates to the vector pComb3HSS containing a DNA according to the invention, wherein the expression of the gp III protein is suppressed or inhibited by deleting the DNA molecule encoding said gp III protein or by a stop codon between the gene coding for a a polypeptide containing the heterologous protein and the protein III gene.

Preferably, a method according to the invention is also characterised in that the heterologous protein is selected from human tissue plasminogen activator (tPA) or a fragment, a functional variant, an allelic variant, a subunit, a chemical derivative, a fusion protein or a glycosylation variant therof. Such fragments, allelic variants, functional variants, variants based on the degenerative nucleic acid code, fusion proteins with an tPA protein according to the invention, chemical derivatives or a glycosylation variant of the tPA proteins according to the invention may include one, several or all of the following domains or subunits or variants thereof:

1. Finger domain (4–50)
2. Growth factor domain (50–87)
3. Kringle 1 domain (87–176)
4. Kringle 2 domain (176–262)
5. Protease domain (276–527)

The numbering/naming of the domains is according to Genbank accession number GI 137119 or *Nature* 301(5897): 214–221 (1983).

More preferably, a method according to the invention is also characterised in that the heterologous protein is selected from the Kringle 2 (Barbas, C. F. III, and Wagner, J., *Comp. Meth. Enzymol.* 8: 94–103 (1995)) plus Serine protease (Bennett, W. F., et al., *J Biol Chem.* 266:5191–5201 (1991)) K2S variant of human tissue plasminogen activator or a fragment, a functional variant, an allelic variant, a subunit, a chemical derivative, a fusion protein or a glycosylation variant therof.

More preferably, a method according to the invention is also characterised in that the vector is a phagemid vector comprising the DNA coding for OmpA signal peptide and the DNA coding for gpIII.

The following example is intended to aid the understanding of the invention and should in no way be regarded as limiting the scope of the invention.

EXAMPLES

Example 1

Materials and Methods

Primer Design. In order to amplify a specific part of tPA gene, a pair of primers sK2/174 [5'GAGGAGGAGGTGGCCCAGGCGGCCTCTGAGGG AAACAGTGAC 3'] (SEQ ID NO:6) and ASSP [5' GAG-GAGGAGCTGGC CGGCCTGGCCCGGTCGCATGT-TGTCACG 3'] (SEQ ID NO:7) were synthesized (Life Technologies, Grand Island, N.Y.). These primers were designed based on the human tPA gene retrieved from NCBI databases (g137119). They were synthesized with Sfi I end cloning sites (underlined) in such a way that the reading frame from the ATG of the gpIII gene in phagemid vector, pComb3HSS, will be maintained throughout the inserted sequence.

Another primer set for site-directed mutagenesis was designed to anneal at the sequence situated between K2S gene and gene III in pComb3H-K2S. The sequence of primers with mutation bases (underlined) for generating a new stop codon were MSTPA [5' ACATGCGACCGTGA-CAGGCCGGCC AG 3'] (SEQ ID NO:8) and MASTPA [5' CTGGCCGGCCTGTCACGGTCG CATGT 3'] (SEQ ID NO:9).

Amplification of K2S Gene by PCR. One µg sK2/174 and ASSP primers together with 50 ng of p51-3 template (obtained from Dr. Hiroshi Sasaki, Fujisawa Pharmaceutical, Japan) were suspended in 100 µl PCR mixture. An amount of 2.5 U Taq polymerase (Roche Molecular Biochemicals, Indianapolis, Ind.) was finally added to the solution. The titrated amplification condition was initiated with jump start at 85° C. for 4 min, then denaturation at 95° C. for 50 sec, annealing at 42° C. for 50 sec, extension at 72° C. for 1.5 min. Thirty five rounds were repeatedly performed. The mixture was further incubated at 72° C. for 10 min. The amplified product of 1110 bp was subsequently purified by QIAquick PCR Purification Kit (QIAGEN, Hilden, Germany). The correctness of purified product was confirmed by restriction enzymes.

Construction of Phagemid Expressing K2S. The purified PCR product of K2S and pComb3HSS phagemid (kindly provided by Dr. Carlos F. Barbas, Scripps Institute, USA) were digested with Sfi I (Roche Molecular Biochemicals, Indianapolis, Ind.) to prepare specific cohesive cloning sites. Four µg of the purified PCR product was digested with 60 U of Sfi I at 50° C. for 18 h. For pComb3HSS, 20 µg of phagemid vectors were treated with 100 U of Sfi I. Digested products of purified PCR product of K2S and pComb3HSS (~3300 bp) were subsequently gel-purified by the QIAquick Gel Extraction Kit (QIAGEN, Hilden, Germany). T4 ligase (Roche Molecular Biochemicals, Indianapolis, Ind.) of 5 U were introduced to the mixture of 0.7 µg of purified Sfi I-digested pComb3HSS and 0.9 µg of purified Sfi I-digested PCR product. Ligation reaction was incubated at 30° C. for 18 h. The newly constructed phagemid was named pComb3H-K2S.

Transformation of XL-1 Blue. Two hundred µl of $CaCl_2$ competent *E. coli* XL-1 Blue (Stratagene, La Jolla, Calif.) were transformed with 70 ng of ligated or mutated product. The transformed cells were propagated by spreading on LB agar containing 100 µg/ml ampicillin and 10 µg/ml tetracycline (Sigma, Saint Louis, Mo.). After cultivation at 37° C. for 18 h several antibiotic resistant colonies were selected for plasmid minipreps by using the alkaline lysis method. Each purified plasmid was subjected to Sfi I restriction site analysis. A transformant harboring plasmid with the correct Sfi I restriction site(s) was subsequently propagated for 18 h at 37° C. in 100 ml LB broth with ampicillin 100 µg/ml and tetracycline 10 µg/ml. A plasmid maxiprep was performed using the QIAGEN Plasmid Maxi Kit (QIAGEN, Hilden, Germany). The purified plasmid was reexamined for specific restriction sites by Sfi I and sequenced by AmpliTaq DNA Polymerase Terminator Cycle Sequencing Kit (The Perkin-Elmer Corporation, Forster City, Calif.).

Site-Directed Mutagenesis of pComb3H-K2S. 10 ng of pComb3H-K2S template were mixed with 125 ng of MSTPA and MASTPA primers. PfuTurbo DNA polymerase (Stratagene, LA Jolla, Calif.) of 2.5 U was added to the mixture for cycle amplification. The reaction started with one round of 95° C. for 30 sec. Then it was followed by 16 rounds consisting of 95° C. for 30 sec, 55° C. for 1 min, and 68° C. for 9 min. The reaction tube was subsequently placed on ice for 2 min. In order to destroy the template strands, 10 U of Dpn I restriction enzyme (Stratagene, LA Jolla, Calif.) were added to the amplification reaction and incubated for 1 h at 37° C. This synthesized product (MpComb3H-K2S) was further used to transform *E. coli* XL-1 Blue.

Preparation of Phage-Display Recombinant-K2S. After pComb3H-K2S was transformed to *E. coli* XL-1 Blue, the phage display technique was performed. A clone of pComb3H-K2S transformed *E. coli* XL-1 Blue was propagated in 10 ml super broth containing ampicillin 100 µg/ml and tetracycline 10 µg/ml at 37° C. until the O.D. [600 nm] of 1.5 was reached. The bacterial culture was subsequently propagated in 100 ml of the same medium and culture for 2 h. An amount of $10^{12}$ pfu of VCSM13 helper phage (Stratagene, La Jolla, Calif.) was used to infect the transformed *E. coli* XL-1 Blue. After 3 h incubation, kanamycin at a final concentration of 70 µg/ml final concentration was added to culture. The culture was left shaking (200 RPM) for 18 h at 37° C. Bacteriophages which harbored K2S on gpIII (K2S-φ) were then harvested by adding 4% w/v PEG MW 8000 (Sigma, Saint Louis, Mo.) and 3% w/v NaCl. Finally, the harvested phage was resuspended in 2 ml PBS pH 7.4. The phage number was determined by infecting *E. coli* XL-1 Blue. The colony-forming unit per milliliter (cfu/ml) was calculated as described previously (Lobel, L. I., et al., *Endocrinology.* 138:1232–1239 (1997)).

Expression of Recombinant-K2S in Shaker Flasks. MpComb3H-K2S transformed XL-1 Blue was cultivated in 100 ml super broth (3% w/v tryptone, 2% w/v yeast extract and 1% w/v MOPS) at pH 7.0 in the presence of ampicillin (100 μg/ml) at 37° C. until an O.D. [600 nm] of 0.8 was reached. Subsequently, the protein synthesis was induced by 1 mM of IPTG (Promega, Madison, Wis.). The bacteria were further cultured shaking (200 RPM) for 6 h at 30° C. The culture supernatant was collected and precipitated with 55% saturated ammonium sulfate (Soeda, S., et al., *Life Sci.* 39:1317–1324 (1986)). The precipitate was reconstituted with PBS, pH 7.2, and dialysed in the same buffer solution at 4° C. for 18 h. Periplasmic proteins from bacterial cells were extracted by using a chloroform shock as previously described by Ames et al. (Ames, G. F., et al., *J. Bacteriol.* 160:1181–1183 (1984)).

Immunoassay Quantification of Recombinant-K2S. In order to detect r-K2S, solid phase was coated with monoclonal anti-kringle 2 domain (16/B) (generously provided by Dr. Ute Zacharias, Central Institute of Molecular Biology, Berlin-Buch, Germany). The standard ELISA washing and blocking processes were preformed. Fifty μl of $10^{11}$ cfu/ml of K2S-φ or secretory r-K2S were added into each anti-kringle 2 coated well. Antigen-antibody detection was carried out as follows. Either sheep anti-M13 conjugated HRP (Pharmacia Biotech, Uppsala, Sweden) or sheep anti-tPA conjugated HRP (Cedarlane, Ontario, Canada), was added to each reaction well after the washing step. The substrate TMB was subjected to every well and the reaction was finally ceased with $H_2SO_4$ solution after 30 min incubation. The standard melanoma tPA 86/670 (National Institute for Biological Standards and Control, Hertfordshine, UK) was used as positive control.

Amidolytic Activity Assay. A test kit for the detection of tPA amidolytic activity was purchased from Chromogenix (Molndal, Sweden). The substrate mixture containing plasminogen and S-2251 was used to determine serine protease enzymatic activity. The dilution of $10^{-2}$ of each ammonium precipitated sample was assayed with and without stimulator, human fibrinogen fragments. The assay procedure was according to the COASET t-PA manual.

SDS-PAGE and Immunoblotting. The dialysed precipitate-product from culture supernatant was further concentrated 10 folds with centricon 10 (AMICON, Beverly, Mass.). The concentrated sample was subjected to protein separation by SDS-PAGE, 15% resolving gel, in the reducing buffer followed by electroblotting to nitrocellulose. The nitrocellulose was then blocked with 4% skimmed milk for 2 hr. In order to detect r-K2S, a proper dilution of sheep anti-tPA conjugated HRP was applied to the nitrocellulose. The immunoreactive band was visualized by a sensitive detection system, Amplified Opti-4CN kit (BIORAD, Hercules, Calif.).

Copolymerized Plasminogen Polyacrylamide Gel Electrophoresis. An 11% resolving polyacrylamide gel was copolymerized with plasminogen and gelatin as previously described by Heussen, C., and Dowdle, E. B., *Anal. Biochem.* 102:196–202 (1980). The stacking gel was prepared as 4% concentration without plasminogen and gelatin. Electrophoresis was performed at 4° C. at a constant current of 8 mA. The residual SDS in gel slab was removed after gentle shaking at room temperature for 1 h in 2.5% Triton X-100. Then the gel slab was incubated in 0.1 M glycine-NaOH, pH 8.3, for 5 h at 37° C. Finally, the gel slab was stained and destained by standard Coomassie brilliant blue (R-250) dying system. The location of the peptide harboring enzymatic activity was not stained by dye in contrast to blue-paint background.

Results

Figure 2:
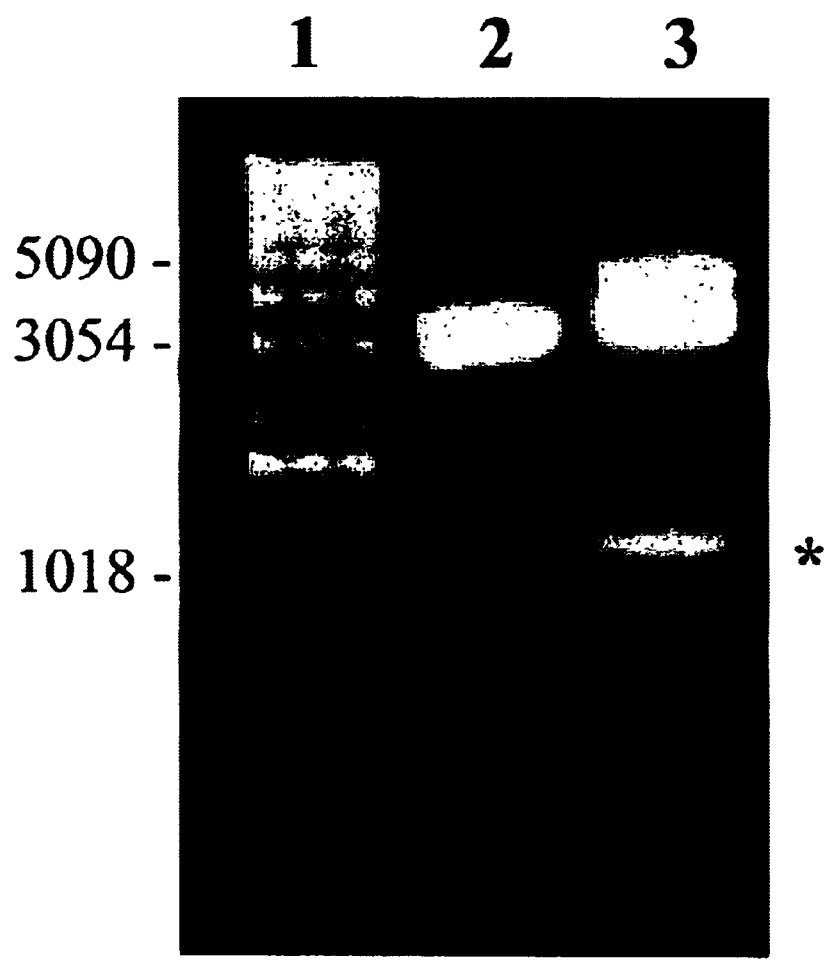
FIG. 2. Identification of inserted K2S gene at 1110 bp (*) after Sfi I digested pComb3H-K2S was demonstrated in lane 3. Lane 1 shows 1 kb marker. Lane 2 was loaded with uncut pComb3H-K2S. The electrophoresis was performed on a 1% agarose gel.
Figure 3:
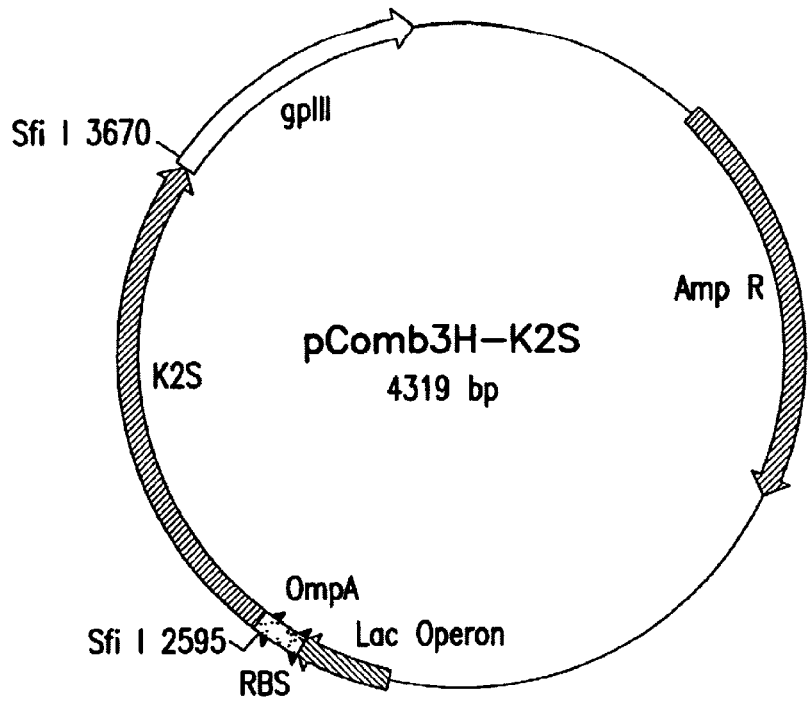
FIG. 3. Scheme of pComb3H-K2S showing two Sfi I cloning sites into which the K2S gene was inserted. Signal sequence (OmpA), ribosome binding site (RIBS), lac promotor, and gpIII gene are also depicted.

Construction of K2S Gene Carrying Vector. From the vector p51-3 we amplified the kringle 2 plus ther serine protease portion of tPA ($Ser^{174}$ in kringle 2 domain to $Pro^{527}$ in the serine protease) using primers sK2/174 and ASSP. The amplified 1110 bp product was demonstrated by agarose gel electrophoresis (FIG. 1, lane 2) and was inserted into pComb3HSS phagemid by double Sfi I cleavage sites on 5' and 3' ends in the correct reading frame. Thus a new vector, pComb3H-K2S, harboring the K2S was generated. In this vector K2S is flanked upstream by the OmpA signal sequence and downstream by gpIII. The correct insertion of K2S was verified both by restriction analysis with Sfi I (FIG. 2, lane 3), PCR-anaysis (demonstration of a single band at 1110 bp), and DNA sequencing. The schematic diagram of pComb3H-K2S map is given in FIG. 3.

Phage-Displayed r-K2S. VCSM13 filamentous phage was used to infect pComb3H-K2S transformed *E. coli* XL-1 Blue, X[K2S]. VCSM13 was propagated and incorporated the K2S-gpIII fusion protein during the viral packaging processes. The harvested recombinant phage (K2S-φ) gave a concentration of $5.4 \times 10^{11}$ cfu/ml determined by reinfecting *E. coli* XL-1 Blue with PEG-precipitated phages. These recombinant phage particles were verified for the expression of r-K2S by sandwich ELISA. The phage-bound heterologous K2S protein was recognized by the monoclonal anti-kringle 2 antibody (16/B) by using sheep anti-tPA conjugated HRP antibody detection system. The absorbance of this assay was 1.12±0.03 (Table 1). The amount of K2S detectable on $10^{12}$ phage particles is equal to 336 ng of protein in relation to the standard melanoma tPA. In order to corroborate that K2S-gpIII fusion protein was associated with phage particles, sheep anti-tPA conjugated HRP antibody was substituted by sheep anti-M13 antibody conjugated HRP. This immuno-reaction exhibited an absorbance of 1.89±0.07 (Table 1). In contrast, if the capture antibody was sheep anti-M13 antibody, extremely low K2S was observed with sheep anti-tPA antibody conjugated HRP; the absorbance was only 0.17±0.01 (Table 1). This suggested that only a minority of purified phage particles carried K2S-gpIII fusion protein. VCSM13 prepared from non-transformed *E. coli* XL-1 Blue was used as a negative control.

Figure 4:
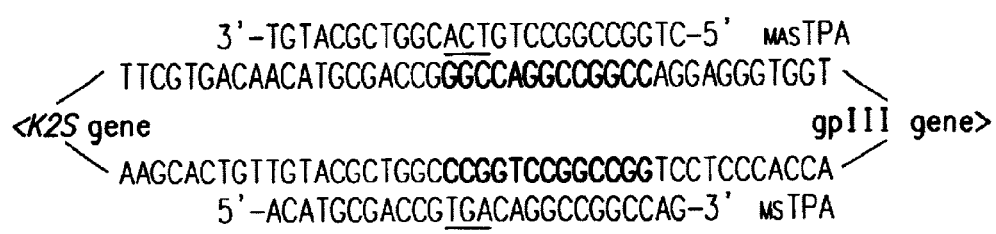
FIG. 4. Schematic diagram of the mutation site at the junction between the K2S and gpIII genes on pComb3H-K2S. The annealing site of pComb3H-K2S is bound with a set of mutation primers (MSTPA and MASTPA) containing modified oligonucleosides (underlined). After performing the cycle amplification, the Sfi I site 1 (in bold) is modified and lost in the newly synthesized strand.
Figure 5:
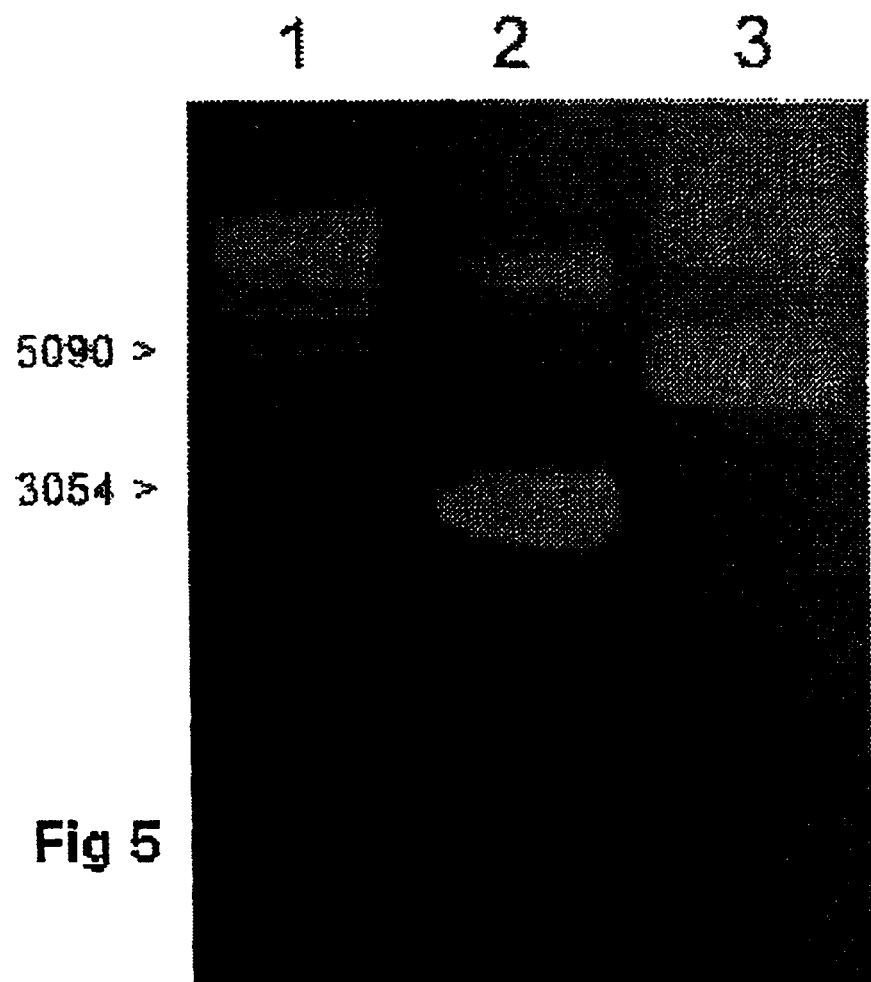
FIG. 5. Characterization of newly synthesized MpComb3H-K2S by the Sfi I restriction enzyme. A single band at 4319 bp that refers to a single cleavage site of MpComb3H-K2S is observed in lane 3. No inserted K2S band at 1110 bp can be visualized. Lane 1 shows 1 kb marker. Lane 2 was loaded with uncut MpComb3H-K2S. The electrophoresis was performed on a 1% agarose gel.

Construction of MpComb3H-K2S. We generated a stop codon between K2S and gpIII in pComb3H-K2S with the aid of the mutagenic primers (MSTPA and MASTPA) (FIG. 4). In order to enrich the newly synthesized and mutated MpComb3H-K2S, the cycle amplification mixture was thoroughly digested with Dpn I to degrade the old dam methylated pComb3H-K2S template (Dpn I prefers dam methylated DNA). After transforming of *E. coli* XL-1 Blue with MpComb3H-K2S, a transformant XM[K2S] was selected for further study. As a consequence of bp substitution, one Sfi I cleavage site close to the 3' end of K2S gene was lost after site-directed mutagenesis. A linear version of Sfi I cleaved MpComb3H-K2S was observed at 4319 bp without the appearance of inserted K2S gene fragment (FIG. 5, lane 3). Thus, the K2S gene encoding by MpComb3H-K2S was expressed in non-gpIII fusion form in *E. coli* XM[K2S].

TABLE 1

Detection of r-K2S molecule in phage preparation by sandwich ELISA

| | Tracer antibody (conjugated HRP) | | | |
|---|---|---|---|---|
| | Anti-tPA | | Anti-M13 | |
| Capture antibody | K2S-φ | VCSM13[a] | K2S-φ | VCSM13 |
| Anti-kringle 2[b] | 1.12 ± 0.04[c] | 0.12 ± 0.03 | 1.89 ± 0.02 | 0.16 ± 0.02 |
| Anti-M13 | 0.17 ± 0.01 | 0.14 ± 0.05 | 1.91 ± 0.02 | 1.88 ± 0.03 |

[a]VCSM13 was harvested from XL-1 Blue transformed with pComb3HSS.
[b]Mouse monoclonal anti-kringle 2 (16/B) was used. The other antibodies were prepared from sheep immunoglobulin.
[c]Value is mean of absorbance of each sample which was assayed in triplicate.

Expression and Purification of K2S. K2S expression in *E. coli* XM[K2S] was induced by IPTG. r-K2S was detectable by using ELISA both in the periplasmic space and in the culture supernatant. The amount of the heterologous protein in each preparation was determined by sandwich ELISA and related to the standard tPA. From 100 ml of the bacterial culture in shaker flask with the O.D. [600 nm] of 50, the periplasmic fraction yielded 1.38 µg of r-K2S (approximately 32%) whereas 2.96 µg of r-K2S (approximately 68%) was obtained in the ammonium precipitated culture supernatant. Sandwich ELISA was used to verify the PEG precipitated phage from VCSM13 infected *E. coli* XM[K2S]. No r-K2S captured by monoclonal anti-kringle 2 antibody was detected by anti-M13 conjugated HRP, indicating that K2S is not presented on the phage particles if gpIII is missing.

Amidolytic Activity Measurement. If serine protease domain is present in the sample, plasminogen will be converted to plasmin. The produced plasmin will further digest the S-2251 substrate to a colour product, p-nitroaniline, which has a maximum absorbance at 405 nm. The specific activity of the recombinant product is in accord with the absorbance. The fibrinogen-dependent enzymatic activity of each sample i.e. K2S-φ, periplasmic r-K2S or culture supernatant r-K2S, was evaluated and compared. Both K2S-φ and periplasmic r-K2S illustrated notably low enzymatic activity, which was below the sensitivity of the test (0.25 IU/ml). The culture supernatant r-K2S gave the fibrinogen-dependent enzymatic activity of 7 IU/ml. Thus, from 100 ml culture we obtained a total of 700 IU enzymatic activity. Without fibrinogen no enzymatic activity of the r-K2S purified from culture supernatant was observed—whereas standard melanoma tPA showed some activity.

Figure 6:
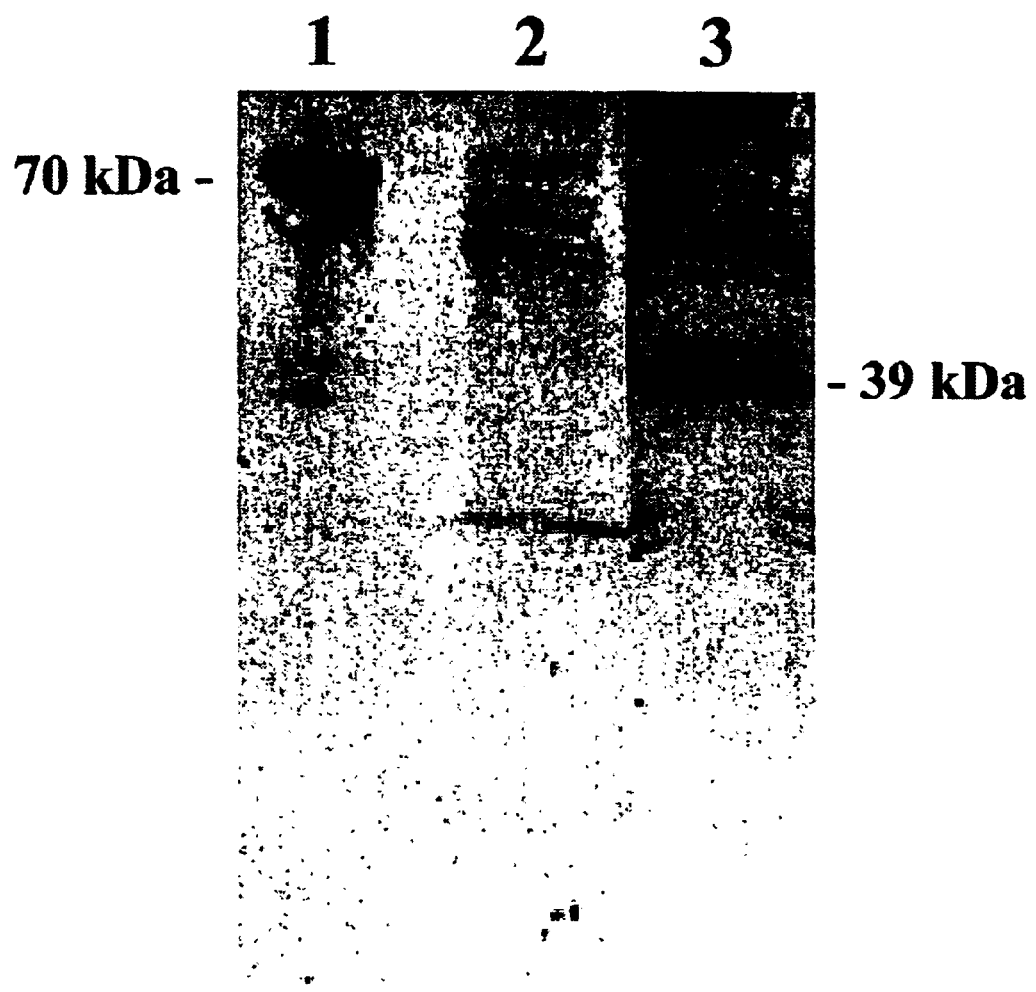
FIG. 6. Identification of immunological reactive band with of recombinant protein purified from *E. coli* XM[K2S] culture supernatant with sheep anti-tPA conjugated HRP. Lane 1 was loaded with 40 ng of standard melanoma tPA (86/670), which showed the reactive band at 70 kDa. The partially purified and concentrated culture supernatants from non-transformed *E. coli* XL1-Blue and *E. coli* XM[K2S] were applied to lane 2 and 3 respectively. The distinct reactive band was particularly demonstrated in lane 3 at 39 kDa.

Demonstration of Recombinant Protein by Immunoblotting. Partially purified K2S from culture supernatant of *E. coli* XM[K2S] revealed a molecular mass of 39 kDa by using sheep anti-tPA antibodies (FIG. 6). The negative control, partially purified culture supernatant of non-transformed *E. coli* XL1-Blue, contained no reactive band with a similar size.

Figure 7:
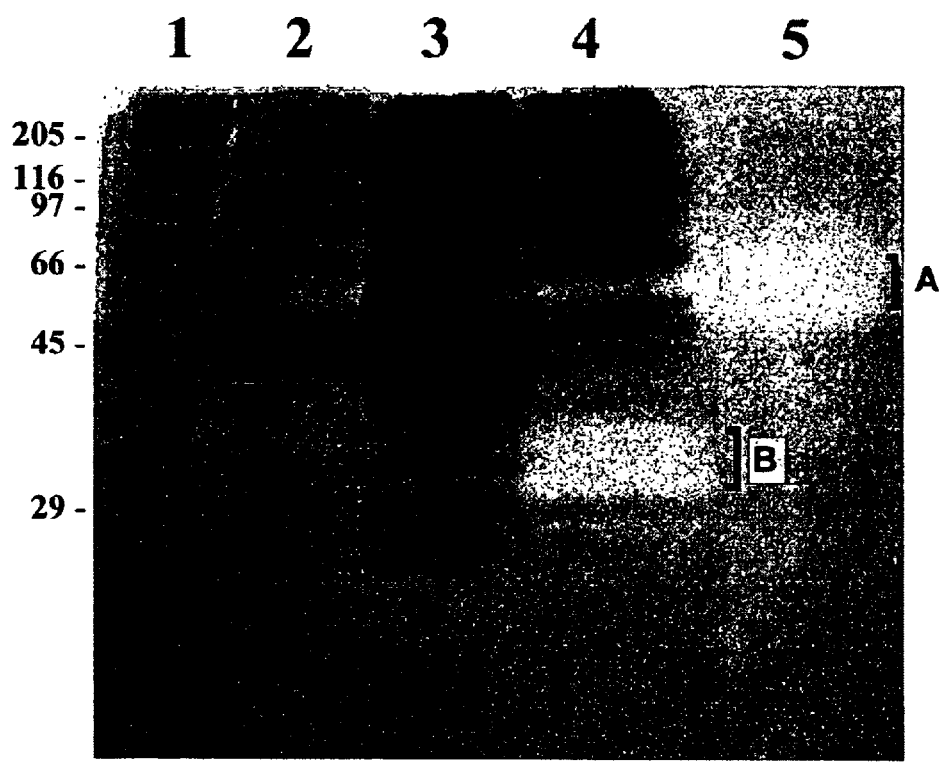
FIG. 7. Molecular weight determination of extracellular r-K2S harboring active serine protease domain by copolymerized plasminogen polyacrylamide gel electrophoresis. Lane 1 contained the indicated molecular weight standards ($\times 10^{-3}$), SDS-6H (Sigma, Saint Louis, Mo.). Fifty μg of the 55% saturated ammonium sulfate precipitated culture supernatant of *E. coli* XL-1 Blue, *E. coli* Xl-1 Blue transformed with pComb3HSS, and *E. coli* XM[K2S] were loaded in lane 2, 3, and 4 respectively. Lane 5 contained 50 mIU of standard melanoma tPA (86/670). Transparent zones of digested plasminogen in polyacrylamide gel are visible only in lane 4 at molecular weight of 34 and 37 kDa (B) and lane 5 at molecular weight of 66 and 72 kDa (A).
Figure 8:
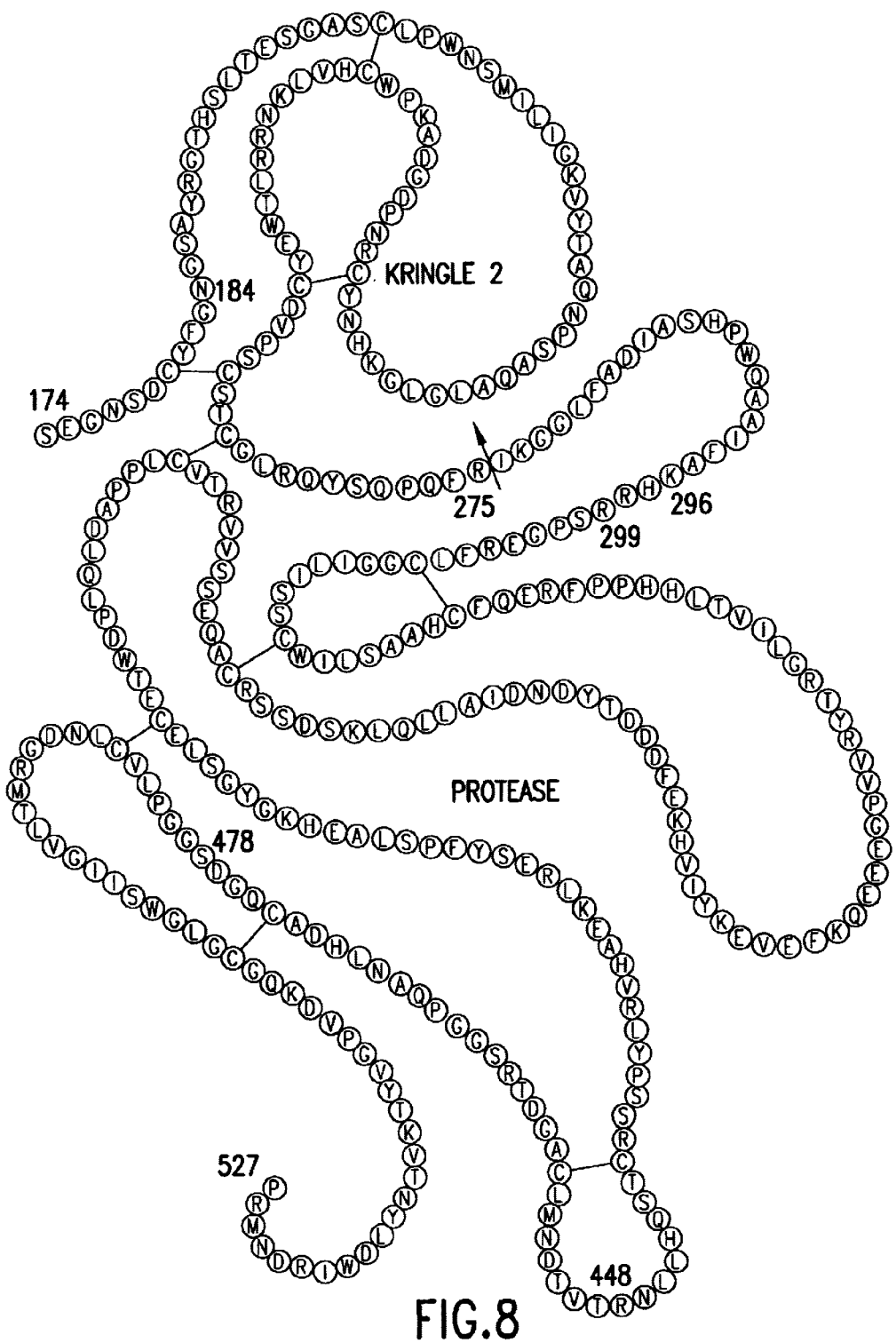
FIG. 8. Structure A. Native K2S molecule from amino acids 174–527 without modification (SEQ ID NO:10).
Figure 9:
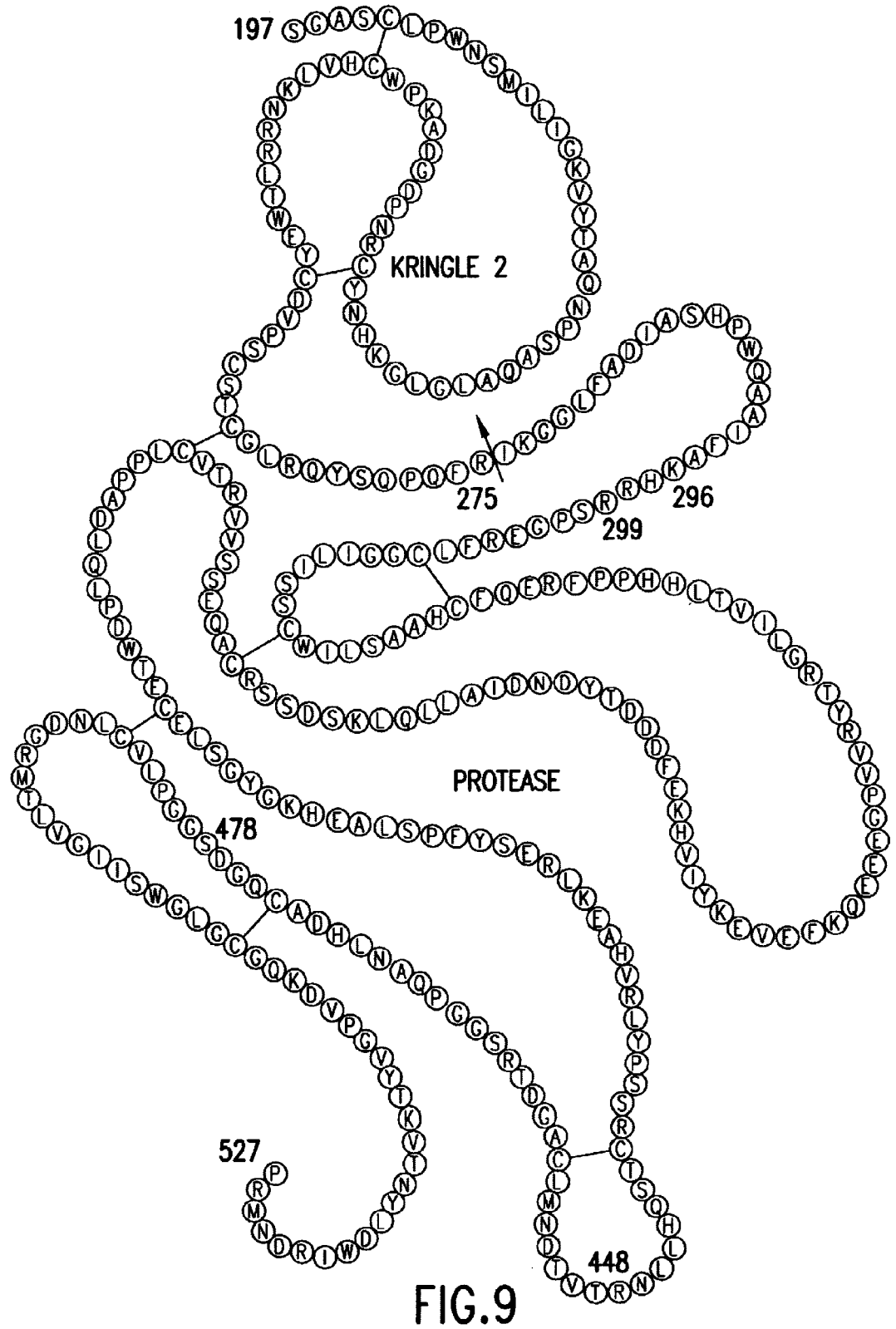
FIG. 9. Structure B-0. Native K2S molecule from amino acids 197–527 without modification. (SEQ ID NO:11)
Figure 10:
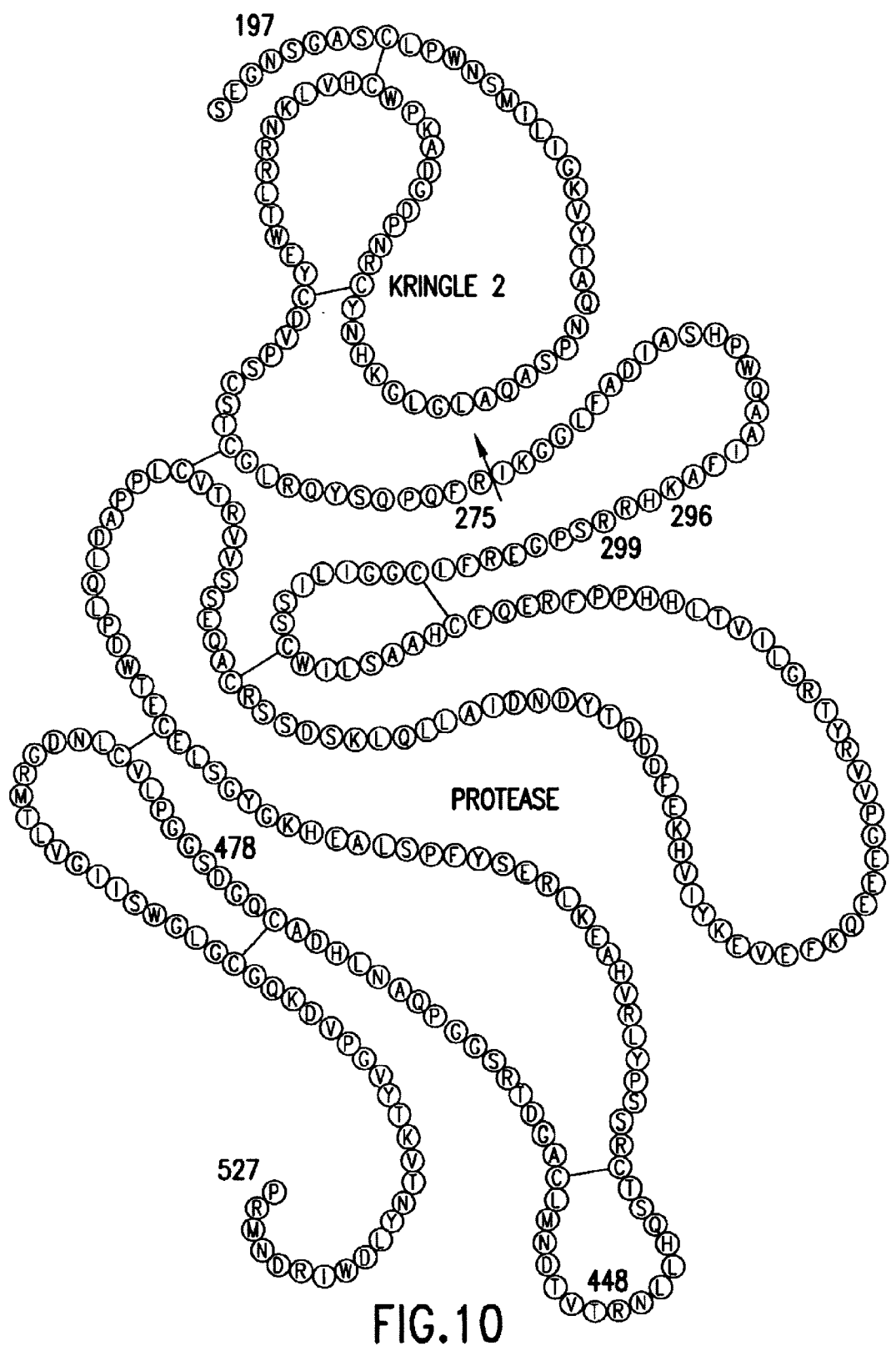
FIG. 10. Structure B-1. K2S molecule from amino acids 193–527, wherein to Structure B-0 of FIG. 9 the amino acids SEGN were added at the N-terminal portion (SEQ ID NO:12).
Figure 11:
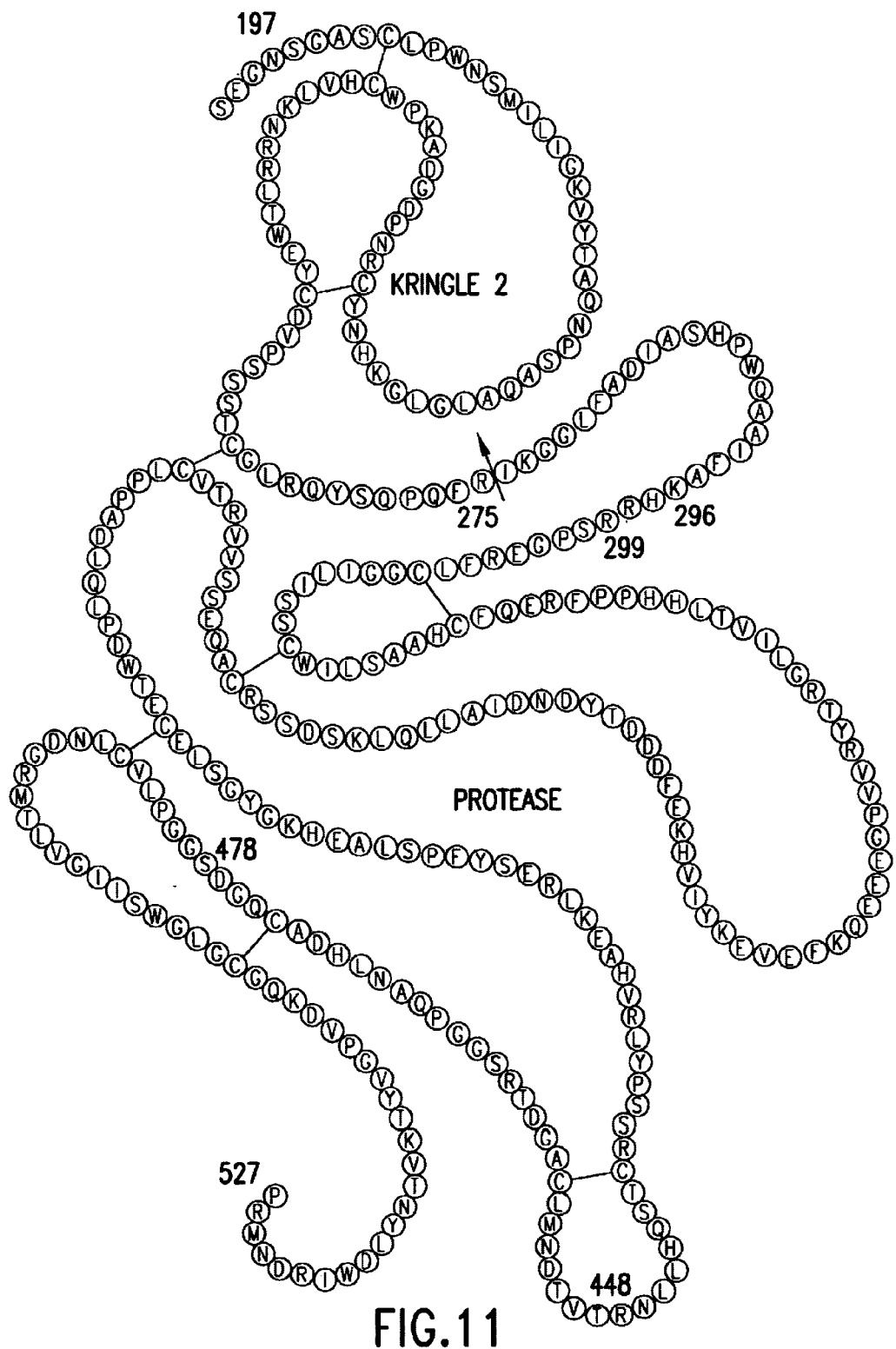
FIG. 11. Structure B-2. K2S molecule from amino acids 193–527, as in FIG. 10, wherein Cys-261 was exchanged for Ser (SEQ ID NO:13).
Figure 12:
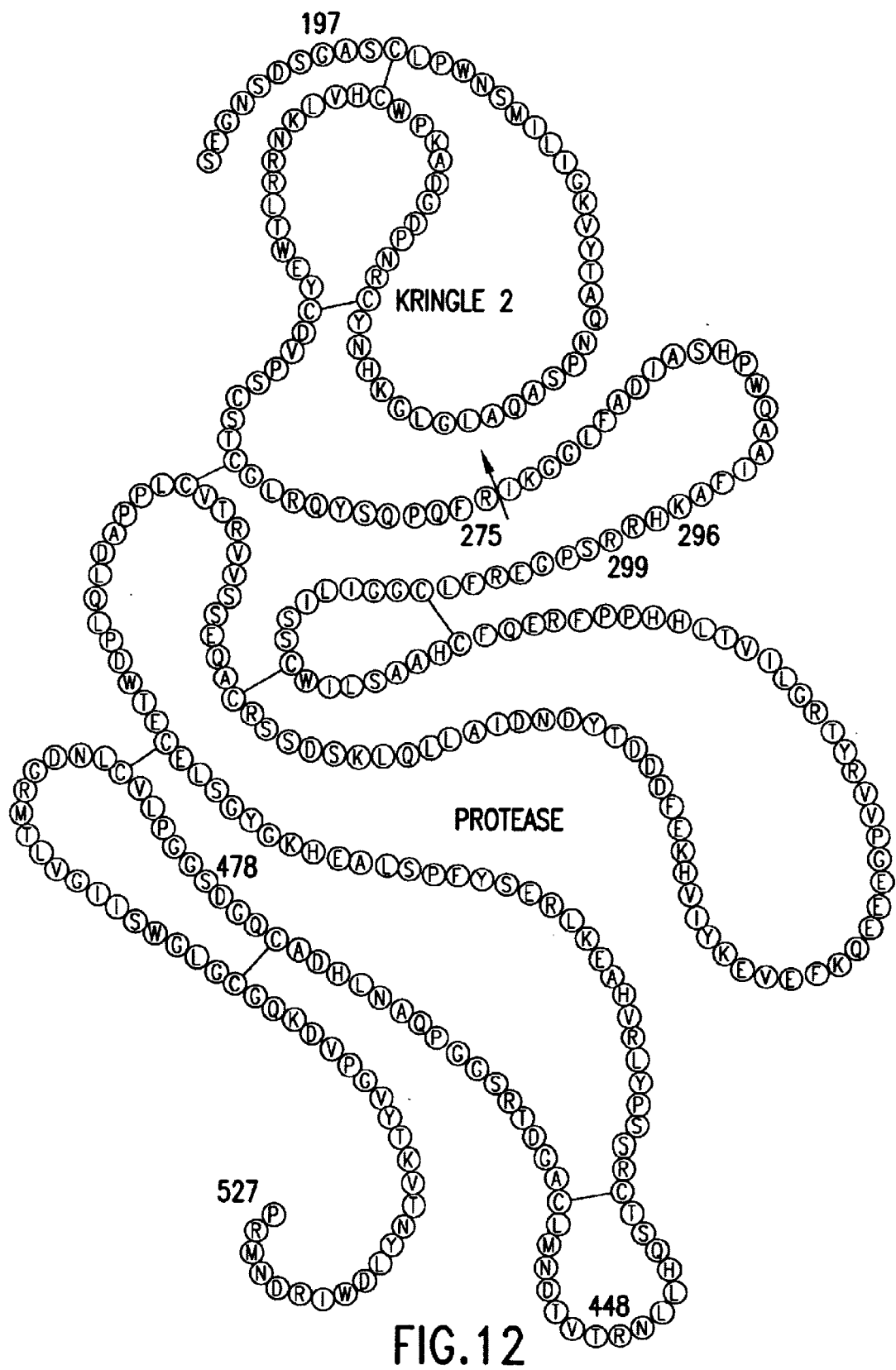
FIG. 12. Structure B-3. K2S molecule from amino acids 191–527, wherein to Structure B-0 of FIG. 9 the amino acids SEGNSD were added at the N-terminal portion (SEQ ID NO:14).
Figure 13:
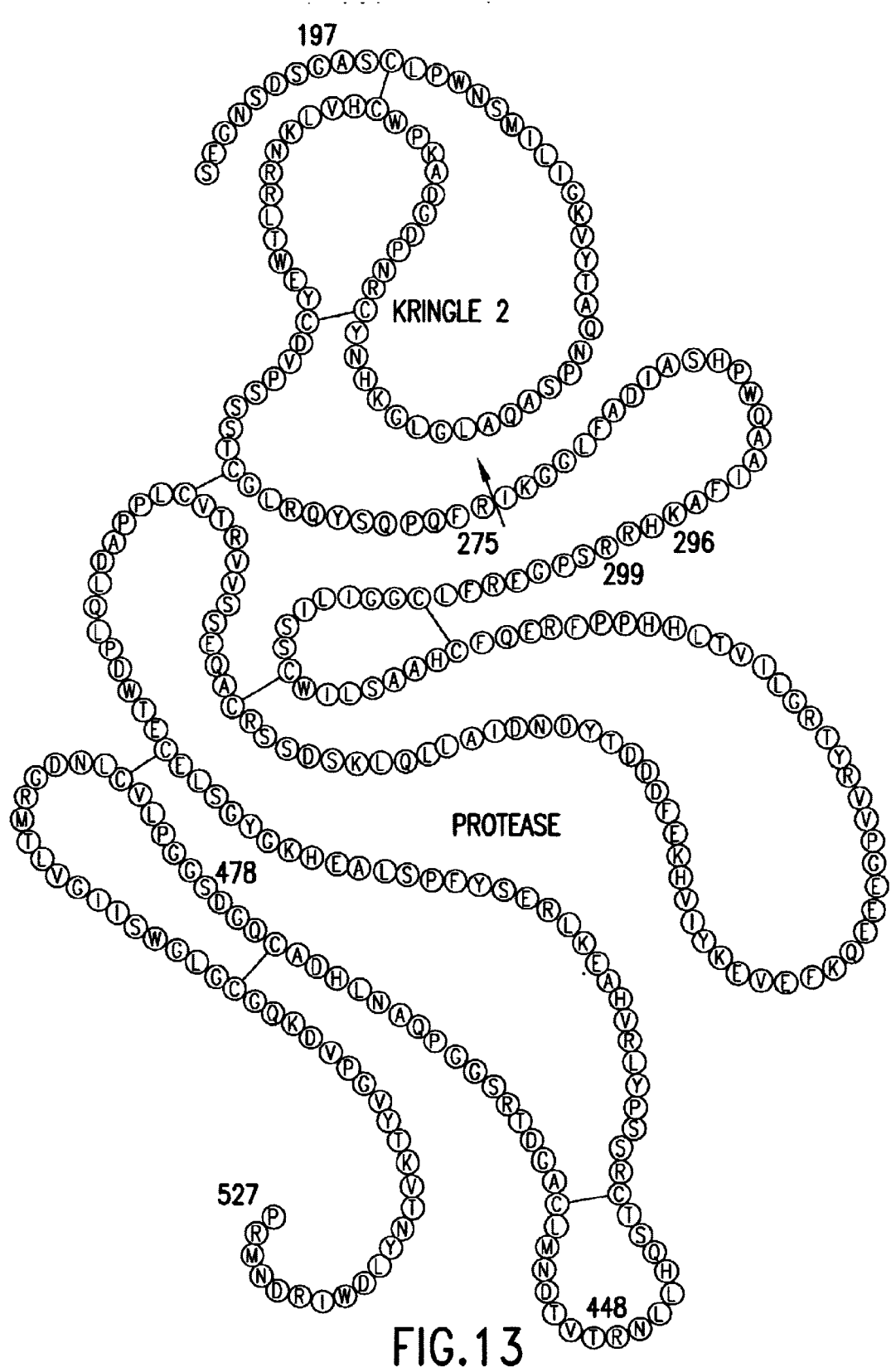
FIG. 13. Structure B-4. K2S molecule from amino acids 191–527, as in FIG. 12, wherein Cys-261 was exchanged for Ser (SEQ ID NO:15).
Figure 14:
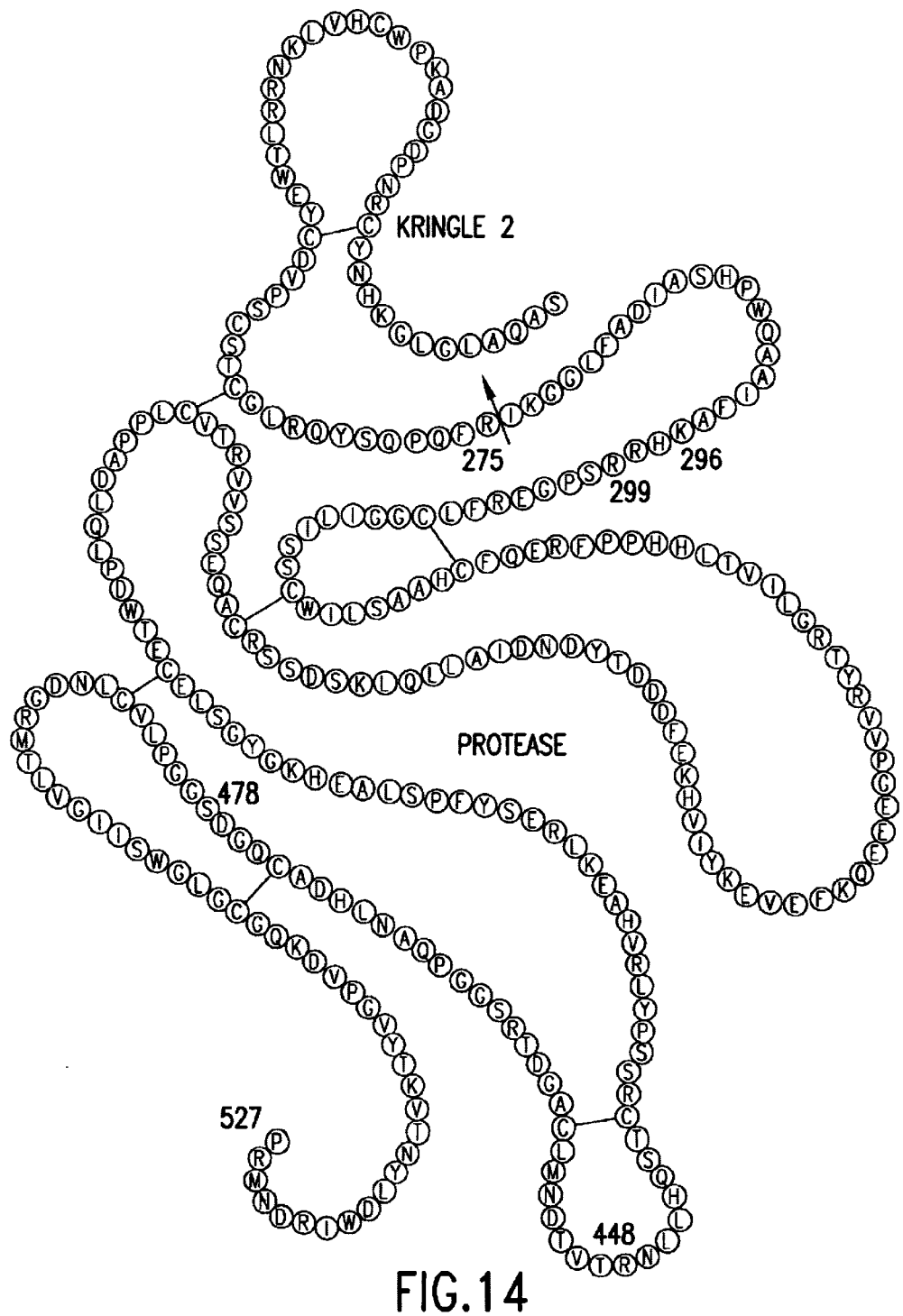
FIG. 14. Structure C. Native K2S molecule from amino acids 220–527 without modification. This molecule may be further modified in a similar manner as disclosed for structure B in FIGS. 10–13 (SEQ ID NO:16).
Figure 15:
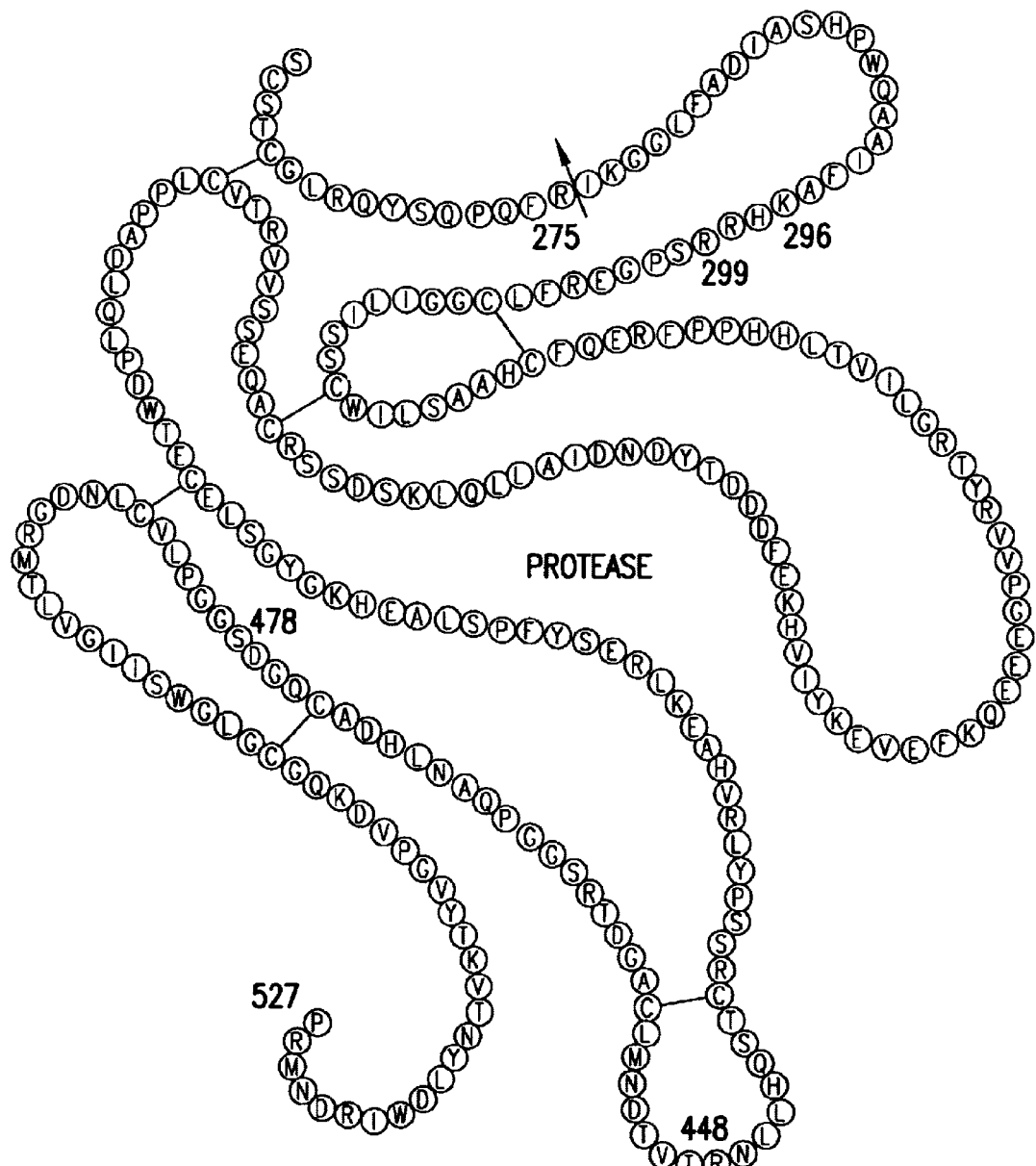
FIG. 15. Structure D. Native K2S molecule from amino acids 260–527 without modification. This molecule may be further modified in a similar manner as disclosed for structure B in FIGS. 10–13 (SEQ ID NO:17).
Figure 16A:
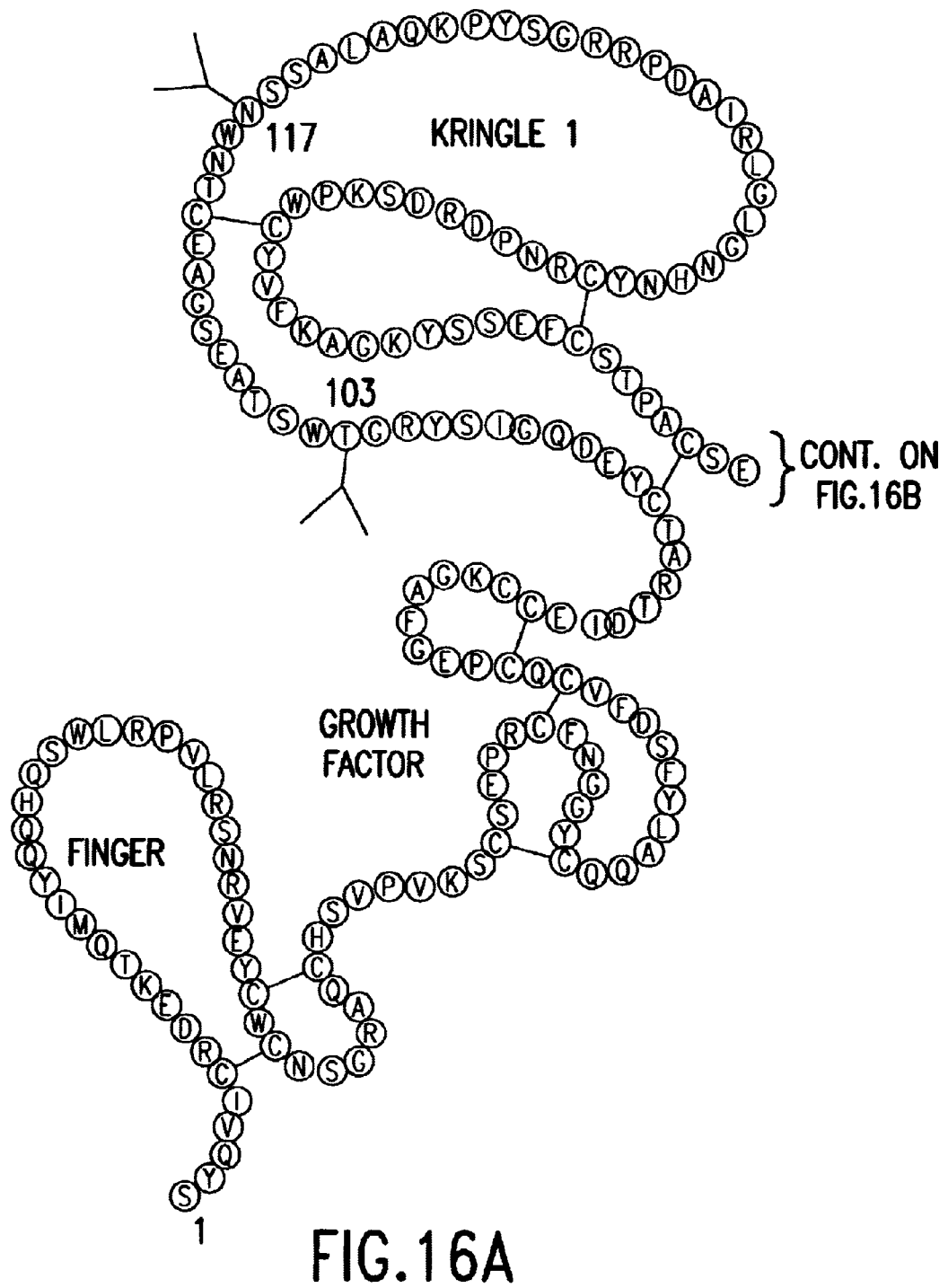
FIG. 16. tPA molecule (SEQ ID NO:18).
Figure 16B:
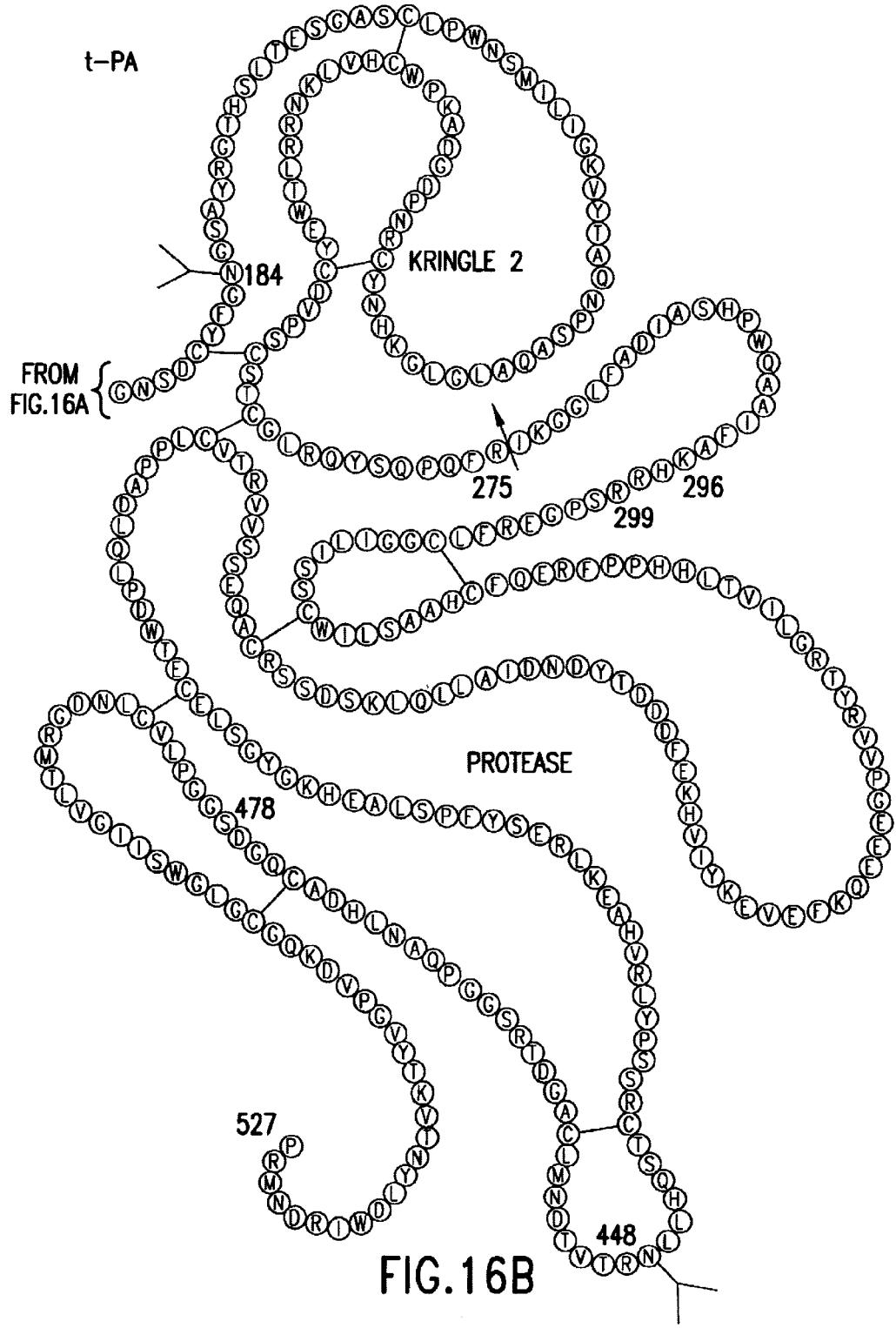

Localization of Active Enzyme by PAGE. The plasminogen has been copolymerized and immobilized with gelatin in the polyacrylamide gel prior to electrophoresis. The ammonium sulfate precipitated culture supernatants of *E. coli* XL-1 Blue, *E. coli* XL-1 Blue transformed with pComb3HSS and *E. coli* XM[K2S] were analyzed (FIG. 7). All samples were processed in non-reducing condition to preserve the correct conformation and activity of the serine protease domain. Transparent areas of serine protease digested plasminogen were observed only in the ammonium sulfate precipitated culture supernatants of *E. coli* XM[K2S] at 34 and 37 kDa positions. The other samples gave no clearing zones. The positive control lane of standard melanoma tPA also demonstrated enzymatic activity at 66 and 72 kDa positions.

What is claimed is:

1. A method for the production of recombinant heterologous protein in prokaryotic cells comprising,
   expressing a vector in said prokaryotic cells said vector comprising:
   (a) DNA encoding an OmpA signal peptide (SEQ ID NO:1);
   (b) DNA encoding said heterologous protein; and
   (c) DNA encoding a peptide selected from the group consisting of SEGN (SEQ ID NO:2) and SEGNSD (SEQ ID NO:3);
      wherein said DNA of (a) is located upstream of said DNA of (c), and said DNA of (b) is located downstream of said DNA of (c);
      wherein said DNAs of (a), (b), and (c) are operably linked; and
   wherein said heterologous protein is secreted extracellularly as an active protein.

2. The method according to claim 1, wherein said heterologous protein is secreted as a correctly folded protein.

3. The method according to claim 1, wherein said DNA of (c) encodes the peptide SEGN (SEQ ID NO:2).

4. The method according to claim 3, wherein said DNA of (c) is TCTGAGGGAAAC (SEQ ID NO:4).

5. The method according to claim 1, wherein said DNA of (c) is encodes the peptide SEGNSD (SEQ ID NO:3).

6. The method according to claim 5, wherein said DNA of (c) is TCTGAGGGAAACAGTGAC (SEQ ID NO:5).

7. The method according to claim 1, wherein the prokaryotic cell is *E. coli*.

8. A method for the production of recombinant heterologous protein in prokaryotic cells comprising:
   a) amplifying DNA encoding said heterologous protein by PCR;
   b) purifying the PCR product;
   c) inserting said PCR product into a vector, wherein said vector comprises:
      (a) DNA encoding an OmpA signal peptide (SEQ ID NO:1);
      (b) DNA encoding a peptide selected from the group consisting of SEGN (SEQ ID NO:2) and SEGNSD (SEQ ID NO:3); and
      (c) DNA encoding gpIII;
         wherein said DNA of (a) is located upstream of said DNA of (b); wherein said PCR product is located downstream of said DNA of (b) and upstream of said DNA of (c); and
         wherein said DNA of (c) is located downstream of said PCR product;
         wherein said DNAs of (a), (b), and (c) and said PCR product are operably linked;
   d) inserting a stop codon between the heterologous protein and gpIII; and
   e) expressing a vector of step (c) in the prokaryotic cells.

9. The method according to claim 8, further comprising:
   f) purifying said heterologous protein.

10. The method according to claim 1, wherein the heterologous protein is tissue plasminogen activator.

11. The method according to claim 1, wherein the vector is a phagemid vector comprising DNA coding for OmpA signal peptide (SEQ ID NO:1) and DNA coding for gpIII.

12. The method according to claim 1, wherein the vector comprises the pComb3HSS phagemid vector.

13. The method according to claim 1, wherein the DNA sequence of OmpA comprises
   ATGAAAAAGACAGCTATCGCGATTG-CAGTGGCACTGGCTGGTTTCGCTACCG TG GCCCAGGCGGCC (SEQ ID NO:1).

14. The method according to claim 1, wherein the DNA sequence of OmpA consists of
   ATGAAAAAGACAGCTATCGCGATTG-CAGTGGCACTGGCTGGTTTCGCTACCG TG GCCCAGGCGGCC (SEQ ID NO:1).

15. The method according to claim 1, wherein the DNA of the heterologous protein is preceded by a lac promoter and/or a ribosomal binding site.

16. A method for the production of recombinant heterologous protein in prokaryotic cells comprising:
   expressing a vector in said prokaryotic cells, said vector comprising;
   (a) DNA encoding an OmpA signal peptide (SEQ ID NO:1);
   (b) DNA encoding the heterologous protein; and
   (c) DNA encoding a peptide selected from the group consisting of SEGN (SEQ ID NO:2) and SEGNSD (SEQ ID NO:3);
      wherein said DNA of (a) is located upstream of said DNA of (c), and said DNA of (b) is located downstream of said DNA of (c); and
      wherein said DNAs of (a), (b), and (c) are operably linked;
   wherein the heterologous protein is a K2S variant; and
   wherein the heterologous protein is secreted extracellularly as an active protein.

17. The method according to claim 16, wherein said heterologous protein is secreted as a correctly folded protein.

18. The method according to claim 16, wherein said DNA of (b) encodes the peptide SEGN (SEQ ID NO:2).

19. The method according to claim 18, wherein said DNA of (b) is TCTGAGGGAAAC (SEQ ID NO:4).

20. The method according to claim 16, wherein said DNA of (b) nucleic acid sequence encodes the peptide SEGNSD (SEQ ID NO:3).

21. The method according to claim 20, wherein said DNA of (b) is TCTGAGGGAAACAGTGAC (SEQ ID NO:5).

22. The method according to claim 16, wherein the prokaryotic cell is *E. coli*.

23. A method for the production of recombinant heterologous protein in prokaryotic cells comprising:
   a) amplifying DNA encoding said heterologous protein by PCR;
   b) purifying the PCR product;
   c) inserting said PCR product into a vector, wherein said vector comprises:
  (a) DNA encoding an OmpA signal peptide (SEQ ID NO:1);
  (b) DNA encoding a peptide selected from the group consisting of SEGN (SEQ ID NO:2) and SEGNSD (SEQ ID NO:3); and
  (c) DNA encoding gpIII;
    wherein said DNA of(a) is located upstream of said DNA of (b); wherein said PCR product is located downstream of said DNA of (b) and upstream of said DNA of (c); and
    wherein said DNA of (c) is located downstream of said PCR product;
  wherein said DNAs of (a), (b), and (c) and said PCR product are operably linked;
d) inserting a stop codon between the heterologous protein and gpIII; and
e) expressing a vector of step (c) in the prokaryotic cells;
wherein the heterologous protein is a K2S variant.

24. The method according to claims 23, further comprising:
  f) purifying said heterologous protein.

25. A method for the production of recombinant K2S in prokaryotic cells comprising:
  expressing a vector in said prokaryotic cells, said vector comprising:
    (a) DNA encoding an OmpA signal peptide (SEQ ID NO:1); and
    (b) DNA encoding K2S;
      wherein said DNA of (a) is located upstream of said DNA of (b); and
      wherein said DNAs of (a) and (b) are operably linked;
  wherein the K2S is secreted extracellularly as an active protein.

26. The method according to claim 16, wherein the vector is a phagemid vector comprising DNA coding for OmpA signal peptide (SEQ ID NO:1) and the peptide SEGN (SEQ ID NO:2) or the peptide SEGNSD (SEQ ID NO:3.

27. The method according to claim 26, wherein the phagemid vector further comprises DNA coding for gpIII.

28. The method according to claim 15, wherein the vector comprises the pComb3HSS phagemid vector.

29. The method according to claim 15, wherein the DNA sequence of OmpA comprises
ATGAAAAAGACAGCTATCGCGATTG- CAGTGGCACTGGCTGGTTTCGCTACCG TG GCCCAGGCGGCC (SEQ ID NO:1).

30. The method according to claim 15, wherein the DNA sequence of OmpA consists of
ATGAAAAAGACAGCTATCGCGATTG- CAGTGGCACTGGCTGGTTTCGCTACCG TG GCCGAGGCGGCC (SEQ ID NO:1).

31. The method according to claim 15, wherein the DNA encoding K2S is preceeded by a lac promotor and/or a ribosomal binding site.

32. The method of claim 15, wherein the K2S variant is selected from the group consisting of SEQ ID NO:10, SEQ ID NO:11, SEQ ID NO:12, SEQ ID NO:13, SEQ ID NO:14, SEQ ID NO:15, SEQ ID NO:16 and SEQ ID NO:17.

33. The method of claim 32, wherein the K2S variant is SEQ ID NO:10.

34. The method of claim 32, wherein the K2S variant is SEQ ID NO:11.

35. The method of claim 32 wherein the K2S variant is SEQ ID NO:12.

36. The method of claim 32, wherein the K2S variant is SEQ ID NO:13.

37. The method of claim 32, wherein the K2S variant is SEQ ID NO:14.

38. The method of claim 32, wherein the K2S variant is SEQ ID NO:15.

39. The method of claim 32, wherein the K2S variant is SEQ ID NO:16.

40. The method of claim 32, wherein the K2S variant is SEQ ID NO:17.

41. The method of claim 23, wherein the K2S variant is selected from the group consisting of SEQ ID NO:10, SEQ ID NO:11, SEQ ID NO:12, SEQ ID NO:13, SEQ ID NO:14, SEQ ID NO:15, SEQ ID NO:16 and SEQ ID NO:17.

42. The method of claim 41, wherein the K2S variant is SEQ ID NO:10.

43. The method of claim 41, wherein the K2S variant is SEQ ID NO:11.

44. The method of claim 41, wherein the K2S variant is SEQ ID NO:12.

45. The method of claim 41, wherein the K2S variant is SEQ ID NO:13.

46. The method of claim 41, wherein the K2S variant is SEQ ID NO:14.

47. The method of claim 41, wherein the K2S variant is SEQ ID NO:15.

48. The method of claim 41, wherein the K2S variant is SEQ ID NO:16.

49. The method of claim 41, wherein the K2S variant is SEQ ID NO:17.

* * * * *

SEQUENCE LISTING

<160> NUMBER OF SEQ ID NOS: 18

<210> SEQ ID NO 1
<211> LENGTH: 66
<212> TYPE: DNA
<213> ORGANISM: Escherichia coli

<400> SEQUENCE: 1

```
atgaaaaaga cagctatcgc gattgcagtg gcactggctg gtttcgctac cgtggcccag    60
gcggcc                                                                66
```

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: N-terminal
      part of K2S molecule

```
<400> SEQUENCE: 2

Ser Glu Gly Asn
  1

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: N-terminal
      part of K2S molecule

<400> SEQUENCE: 3

Ser Glu Gly Asn Ser Asp
  1               5

<210> SEQ ID NO 4
<211> LENGTH: 12
<212> TYPE: DNA
<213> ORGANISM: Artificial Sequence
<220> FEATURE:
<223> OTHER INFORMATION: Description of Artificial Sequence: coding
      sequence of the N-terminal part of K2S molecule

<400> SEQUENCE: 4
tctgagggaa ac                                                           12

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: coding
      sequence of the N-terminal part of K2S molecule

<400> SEQUENCE: 5
tctgagggaa acagtgac                                                     18

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence:
      oligonucleotide sequence

<400> SEQUENCE: 6
gaggaggagg tggcccaggc ggcctctgag ggaaacagtg ac                           42

<210> SEQ ID NO 7
<211> LENGTH: 42
<212> TYPE: DNA
<213> ORGANISM: Artificial Sequence
<220> FEATURE:
<223> OTHER INFORMATION: Description of Artificial Sequence:
      oligonucleotide sequence

<400> SEQUENCE: 7
gaggaggagc tggccggcct ggcccggtcg catgttgtca cg                           42

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence:
```

-continued

```
oligonucleotide sequence

<400> SEQUENCE: 8
acatgcgacc gtgacaggcc ggccag                                           26

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence:
      oligonucleotide sequence

<400> SEQUENCE: 9
ctggccggcc tgtcacggtc gcatgt                                           26

<210> SEQ ID NO 10
<211> LENGTH: 354
<212> TYPE: PRT
<213> ORGANISM: Artificial Sequence
<220> FEATURE:
<223> OTHER INFORMATION: Description of Artificial Sequence: part of the
      recombinant K2S molecule

<400> SEQUENCE: 10
```

Ser Glu Gly Asn Ser Asp Cys Tyr Phe Gly Asn Gly Ser Ala Tyr Arg
  1               5                  10                  15

Gly Thr His Ser Leu Thr Glu Ser Gly Ala Ser Cys Leu Pro Trp Asn
             20                  25                  30

Ser Met Ile Leu Ile Gly Lys Val Tyr Thr Ala Gln Asn Pro Ser Ala
         35                  40                  45

Gln Ala Leu Gly Leu Gly Lys His Asn Tyr Cys Arg Asn Pro Asp Gly
     50                  55                  60

Asp Ala Lys Pro Trp Cys His Val Leu Lys Asn Arg Arg Leu Thr Trp
 65                  70                  75                  80

Glu Tyr Cys Asp Val Pro Ser Cys Ser Thr Cys Gly Leu Arg Gln Tyr
                 85                  90                  95

Ser Gln Pro Gln Phe Arg Ile Lys Gly Gly Leu Phe Ala Asp Ile Ala
            100                 105                 110

Ser His Pro Trp Gln Ala Ala Ile Phe Ala Lys His Arg Arg Ser Pro
        115                 120                 125

Gly Glu Arg Phe Leu Cys Gly Gly Ile Leu Ile Ser Ser Cys Trp Ile
    130                 135                 140

Leu Ser Ala Ala His Cys Phe Gln Glu Arg Phe Pro Pro His His Leu
145                 150                 155                 160

Thr Val Ile Leu Gly Arg Thr Tyr Arg Val Val Pro Gly Glu Glu Glu
                165                 170                 175

Gln Lys Phe Glu Val Glu Lys Tyr Ile Val His Lys Glu Phe Asp Asp
            180                 185                 190

Asp Thr Tyr Asp Asn Asp Ile Ala Leu Leu Gln Leu Lys Ser Asp Ser
        195                 200                 205

Ser Arg Cys Ala Gln Glu Ser Ser Val Val Arg Thr Val Cys Leu Pro
    210                 215                 220

Pro Ala Asp Leu Gln Leu Pro Asp Trp Thr Glu Cys Glu Leu Ser Gly
225                 230                 235                 240

Tyr Gly Lys His Glu Ala Leu Ser Pro Phe Tyr Ser Glu Arg Leu Lys
                245                 250                 255

Glu Ala His Val Arg Leu Tyr Pro Ser Ser Arg Cys Thr Ser Gln His

-continued

```
                    260                 265                 270
Leu Leu Asn Arg Thr Val Thr Asp Asn Met Leu Cys Ala Gly Asp Thr
                275                 280                 285
Arg Ser Gly Gly Pro Gln Ala Asn Leu His Asp Ala Cys Gln Gly Asp
            290                 295                 300
Ser Gly Gly Pro Leu Val Cys Leu Asn Asp Gly Arg Met Thr Leu Val
305                 310                 315                 320
Gly Ile Ile Ser Trp Gly Leu Gly Cys Gly Gln Lys Asp Val Pro Gly
                325                 330                 335
Val Tyr Thr Lys Val Thr Asn Tyr Leu Asp Trp Ile Arg Asp Asn Met
            340                 345                 350
Arg Pro
```

<210> SEQ ID NO 11
<211> LENGTH: 331
<212> TYPE: PRT
<213> ORGANISM: Artificial Sequence
<220> FEATURE:
<223> OTHER INFORMATION: Description of Artificial Sequence: part of the
      recombinant K2S molecule

<400> SEQUENCE: 11

```
Ser Gly Ala Ser Cys Leu Pro Trp Asn Ser Met Ile Leu Ile Gly Lys
1               5                   10                  15
Val Tyr Thr Ala Gln Asn Pro Ser Ala Gln Ala Leu Gly Leu Gly Lys
                20                  25                  30
His Asn Tyr Cys Arg Asn Pro Asp Gly Asp Ala Lys Pro Trp Cys His
            35                  40                  45
Val Leu Lys Asn Arg Arg Leu Thr Trp Glu Tyr Cys Asp Val Pro Ser
        50                  55                  60
Cys Ser Thr Cys Gly Leu Arg Gln Tyr Ser Gln Pro Gln Phe Arg Ile
65                  70                  75                  80
Lys Gly Gly Leu Phe Ala Asp Ile Ala Ser His Pro Trp Gln Ala Ala
                85                  90                  95
Ile Phe Ala Lys His Arg Arg Ser Pro Gly Glu Arg Phe Leu Cys Gly
            100                 105                 110
Gly Ile Leu Ile Ser Ser Cys Trp Ile Leu Ser Ala Ala His Cys Phe
        115                 120                 125
Gln Glu Arg Phe Pro Pro His His Leu Thr Val Ile Leu Gly Arg Thr
130                 135                 140
Tyr Arg Val Val Pro Gly Glu Glu Glu Gln Lys Phe Glu Val Glu Lys
145                 150                 155                 160
Tyr Ile Val His Lys Glu Phe Asp Asp Asp Thr Tyr Asp Asn Asp Ile
                165                 170                 175
Ala Leu Leu Gln Leu Lys Ser Asp Ser Ser Arg Cys Ala Gln Glu Ser
            180                 185                 190
Ser Val Val Arg Thr Val Cys Leu Pro Pro Ala Asp Leu Gln Leu Pro
        195                 200                 205
Asp Trp Thr Glu Cys Glu Leu Ser Gly Tyr Gly Lys His Glu Ala Leu
    210                 215                 220
Ser Pro Phe Tyr Ser Glu Arg Leu Lys Glu Ala His Val Arg Leu Tyr
225                 230                 235                 240
Pro Ser Ser Arg Cys Thr Ser Gln His Leu Leu Asn Arg Thr Val Thr
                245                 250                 255
Asp Asn Met Leu Cys Ala Gly Asp Thr Arg Ser Gly Gly Pro Gln Ala
```

```
                        260                 265                 270
Asn Leu His Asp Ala Cys Gln Gly Asp Ser Gly Gly Pro Leu Val Cys
                275                 280                 285

Leu Asn Asp Gly Arg Met Thr Leu Val Gly Ile Ile Ser Trp Gly Leu
        290                 295                 300

Gly Cys Gly Gln Lys Asp Val Pro Gly Val Tyr Thr Lys Val Thr Asn
305                 310                 315                 320

Tyr Leu Asp Trp Ile Arg Asp Asn Met Arg Pro
                325                 330

<210> SEQ ID NO 12
<211> LENGTH: 339
<212> TYPE: PRT
<213> ORGANISM: Artificial Sequence
<220> FEATURE:
<223> OTHER INFORMATION: Description of Artificial Sequence: part of the
      recombinant K2S molecule (modified)

<400> SEQUENCE: 12

Ser Glu Gly Asn Ser Leu Thr Glu Ser Gly Ala Ser Cys Leu Pro Trp
1               5                   10                  15

Asn Ser Met Ile Leu Ile Gly Lys Val Tyr Thr Ala Gln Asn Pro Ser
                20                  25                  30

Ala Gln Ala Leu Gly Leu Gly Lys His Asn Tyr Cys Arg Asn Pro Asp
            35                  40                  45

Gly Asp Ala Lys Pro Trp Cys His Val Leu Lys Asn Arg Arg Leu Thr
        50                  55                  60

Trp Glu Tyr Cys Asp Val Pro Ser Cys Ser Thr Cys Gly Leu Arg Gln
65                  70                  75                  80

Tyr Ser Gln Pro Gln Phe Arg Ile Lys Gly Gly Leu Phe Ala Asp Ile
                85                  90                  95

Ala Ser His Pro Trp Gln Ala Ala Ile Phe Ala Lys His Arg Arg Ser
            100                 105                 110

Pro Gly Glu Arg Phe Leu Cys Gly Gly Ile Leu Ile Ser Ser Cys Trp
        115                 120                 125

Ile Leu Ser Ala Ala His Cys Phe Gln Glu Arg Phe Pro Pro His His
130                 135                 140

Leu Thr Val Ile Leu Gly Arg Thr Tyr Arg Val Val Pro Gly Glu Glu
145                 150                 155                 160

Glu Gln Lys Phe Glu Val Glu Lys Tyr Ile Val His Lys Glu Phe Asp
                165                 170                 175

Asp Asp Thr Tyr Asp Asn Asp Ile Ala Leu Leu Gln Leu Lys Ser Asp
            180                 185                 190

Ser Ser Arg Cys Ala Gln Glu Ser Ser Val Val Arg Thr Val Cys Leu
        195                 200                 205

Pro Pro Ala Asp Leu Gln Leu Pro Asp Trp Thr Glu Cys Glu Leu Ser
210                 215                 220

Gly Tyr Gly Lys His Glu Ala Leu Ser Pro Phe Tyr Ser Glu Arg Leu
225                 230                 235                 240

Lys Glu Ala His Val Arg Leu Tyr Pro Ser Ser Arg Cys Thr Ser Gln
                245                 250                 255

His Leu Leu Asn Arg Thr Val Thr Asp Asn Met Leu Cys Ala Gly Asp
            260                 265                 270

Thr Arg Ser Gly Gly Pro Gln Ala Asn Leu His Asp Ala Cys Gln Gly
        275                 280                 285
```

```
Asp Ser Gly Gly Pro Leu Val Cys Leu Asn Asp Gly Arg Met Thr Leu
    290                 295                 300

Val Gly Ile Ile Ser Trp Gly Leu Gly Cys Gly Gln Lys Asp Val Pro
305                 310                 315                 320

Gly Val Tyr Thr Lys Val Thr Asn Tyr Leu Asp Trp Ile Arg Asp Asn
                325                 330                 335

Met Arg Pro
```

<210> SEQ ID NO 13
<211> LENGTH: 335
<212> TYPE: PRT
<213> ORGANISM: Artificial Sequence
<220> FEATURE:
<223> OTHER INFORMATION: Description of Artificial Sequence: part of the
      recombinant K2S molecule (modified)

<400> SEQUENCE: 13

```
Ser Leu Thr Glu Ser Gly Ala Ser Cys Leu Pro Trp Asn Ser Met Ile
  1               5                  10                  15

Leu Ile Gly Lys Val Tyr Thr Ala Gln Asn Pro Ser Ala Gln Ala Leu
             20                  25                  30

Gly Leu Gly Lys His Asn Tyr Cys Arg Asn Pro Asp Gly Asp Ala Lys
         35                  40                  45

Pro Trp Cys His Val Leu Lys Asn Arg Arg Leu Thr Trp Glu Tyr Cys
     50                  55                  60

Asp Val Pro Ser Ser Thr Cys Gly Leu Arg Gln Tyr Ser Gln Pro
 65                  70                  75                  80

Gln Phe Arg Ile Lys Gly Gly Leu Phe Ala Asp Ile Ala Ser His Pro
                 85                  90                  95

Trp Gln Ala Ala Ile Phe Ala Lys His Arg Arg Ser Pro Gly Glu Arg
            100                 105                 110

Phe Leu Cys Gly Gly Ile Leu Ile Ser Ser Cys Trp Ile Leu Ser Ala
        115                 120                 125

Ala His Cys Phe Gln Glu Arg Phe Pro Pro His His Leu Thr Val Ile
    130                 135                 140

Leu Gly Arg Thr Tyr Arg Val Val Pro Gly Glu Glu Glu Gln Lys Phe
145                 150                 155                 160

Glu Val Glu Lys Tyr Ile Val His Lys Glu Phe Asp Asp Thr Tyr
                165                 170                 175

Asp Asn Asp Ile Ala Leu Leu Gln Leu Lys Ser Asp Ser Ser Arg Cys
            180                 185                 190

Ala Gln Glu Ser Ser Val Val Arg Thr Val Cys Leu Pro Pro Ala Asp
        195                 200                 205

Leu Gln Leu Pro Asp Trp Thr Glu Cys Glu Leu Ser Gly Tyr Gly Lys
    210                 215                 220

His Glu Ala Leu Ser Pro Phe Tyr Ser Glu Arg Leu Lys Glu Ala His
225                 230                 235                 240

Val Arg Leu Tyr Pro Ser Ser Arg Cys Thr Ser Gln His Leu Leu Asn
                245                 250                 255

Arg Thr Val Thr Asp Asn Met Leu Cys Ala Gly Asp Thr Arg Ser Gly
            260                 265                 270

Gly Pro Gln Ala Asn Leu His Asp Ala Cys Gln Gly Asp Ser Gly Gly
        275                 280                 285

Pro Leu Val Cys Leu Asn Asp Gly Arg Met Thr Leu Val Gly Ile Ile
    290                 295                 300
```

```
Ser Trp Gly Leu Gly Cys Gly Gln Lys Asp Val Pro Gly Val Tyr Thr
305                 310                 315                 320

Lys Val Thr Asn Tyr Leu Asp Trp Ile Arg Asp Asn Met Arg Pro
                325                 330                 335

<210> SEQ ID NO 14
<211> LENGTH: 343
<212> TYPE: PRT
<213> ORGANISM: Artificial Sequence
<220> FEATURE:
<223> OTHER INFORMATION: Description of Artificial Sequence: part of the
      recombinant K2S molecule (modified)

<400> SEQUENCE: 14

Ser Glu Gly Asn Ser Asp Thr His Ser Leu Thr Glu Ser Gly Ala Ser
1               5                   10                  15

Cys Leu Pro Trp Asn Ser Met Ile Leu Ile Gly Lys Val Tyr Thr Ala
                20                  25                  30

Gln Asn Pro Ser Ala Gln Ala Leu Gly Leu Gly Lys His Asn Tyr Cys
            35                  40                  45

Arg Asn Pro Asp Gly Asp Ala Lys Pro Trp Cys His Val Leu Lys Asn
    50                  55                  60

Arg Arg Leu Thr Trp Glu Tyr Cys Asp Val Pro Ser Cys Ser Thr Cys
65                  70                  75                  80

Gly Leu Arg Gln Tyr Ser Gln Pro Gln Phe Arg Ile Lys Gly Gly Leu
                85                  90                  95

Phe Ala Asp Ile Ala Ser His Pro Trp Gln Ala Ala Ile Phe Ala Lys
                100                 105                 110

His Arg Arg Ser Pro Gly Glu Arg Phe Leu Cys Gly Gly Ile Leu Ile
            115                 120                 125

Ser Ser Cys Trp Ile Leu Ser Ala Ala His Cys Phe Gln Glu Arg Phe
130                 135                 140

Pro Pro His His Leu Thr Val Ile Leu Gly Arg Thr Tyr Arg Val Val
145                 150                 155                 160

Pro Gly Glu Glu Glu Gln Lys Phe Glu Val Glu Lys Tyr Ile Val His
                165                 170                 175

Lys Glu Phe Asp Asp Asp Thr Tyr Asp Asn Asp Ile Ala Leu Leu Gln
            180                 185                 190

Leu Lys Ser Asp Ser Ser Arg Cys Ala Gln Glu Ser Ser Val Val Arg
        195                 200                 205

Thr Val Cys Leu Pro Pro Ala Asp Leu Gln Leu Pro Asp Trp Thr Glu
210                 215                 220

Cys Glu Leu Ser Gly Tyr Gly Lys His Glu Ala Leu Ser Pro Phe Tyr
225                 230                 235                 240

Ser Glu Arg Leu Lys Glu Ala His Val Arg Leu Tyr Pro Ser Ser Arg
                245                 250                 255

Cys Thr Ser Gln His Leu Leu Asn Arg Thr Val Thr Asp Asn Met Leu
            260                 265                 270

Cys Ala Gly Asp Thr Arg Ser Gly Gly Pro Gln Ala Asn Leu His Asp
        275                 280                 285

Ala Cys Gln Gly Asp Ser Gly Gly Pro Leu Val Cys Leu Asn Asp Gly
        290                 295                 300

Arg Met Thr Leu Val Gly Ile Ile Ser Trp Gly Leu Gly Cys Gly Gln
305                 310                 315                 320

Lys Asp Val Pro Gly Val Tyr Thr Lys Val Thr Asn Tyr Leu Asp Trp
                325                 330                 335
```

```
Ile Arg Asp Asn Met Arg Pro
            340

<210> SEQ ID NO 15
<211> LENGTH: 343
<212> TYPE: PRT
<213> ORGANISM: Artificial Sequence
<220> FEATURE:
<223> OTHER INFORMATION: Description of Artificial Sequence: part of the
      recombinant K2S molecule (modified)

<400> SEQUENCE: 15

Ser Glu Gly Asn Ser Asp Thr His Ser Leu Thr Glu Ser Gly Ala Ser
 1               5                  10                  15

Cys Leu Pro Trp Asn Ser Met Ile Leu Ile Gly Lys Val Tyr Thr Ala
             20                  25                  30

Gln Asn Pro Ser Ala Gln Ala Leu Gly Leu Gly Lys His Asn Tyr Cys
         35                  40                  45

Arg Asn Pro Asp Gly Asp Ala Lys Pro Trp Cys His Val Leu Lys Asn
     50                  55                  60

Arg Arg Leu Thr Trp Glu Tyr Cys Asp Val Pro Ser Ser Ser Thr Cys
 65                  70                  75                  80

Gly Leu Arg Gln Tyr Ser Gln Pro Gln Phe Arg Ile Lys Gly Gly Leu
                 85                  90                  95

Phe Ala Asp Ile Ala Ser His Pro Trp Gln Ala Ala Ile Phe Ala Lys
            100                 105                 110

His Arg Arg Ser Pro Gly Glu Arg Phe Leu Cys Gly Gly Ile Leu Ile
        115                 120                 125

Ser Ser Cys Trp Ile Leu Ser Ala Ala His Cys Phe Gln Glu Arg Phe
    130                 135                 140

Pro Pro His His Leu Thr Val Ile Leu Gly Arg Thr Tyr Arg Val Val
145                 150                 155                 160

Pro Gly Glu Glu Glu Gln Lys Phe Glu Val Glu Lys Tyr Ile Val His
                165                 170                 175

Lys Glu Phe Asp Asp Asp Thr Tyr Asp Asn Asp Ile Ala Leu Leu Gln
            180                 185                 190

Leu Lys Ser Asp Ser Ser Arg Cys Ala Gln Glu Ser Ser Val Val Arg
        195                 200                 205

Thr Val Cys Leu Pro Pro Ala Asp Leu Gln Leu Pro Asp Trp Thr Glu
    210                 215                 220

Cys Glu Leu Ser Gly Tyr Gly Lys His Glu Ala Leu Ser Pro Phe Tyr
225                 230                 235                 240

Ser Glu Arg Leu Lys Glu Ala His Val Arg Leu Tyr Pro Ser Ser Arg
                245                 250                 255

Cys Thr Ser Gln His Leu Leu Asn Arg Thr Val Thr Asp Asn Met Leu
            260                 265                 270

Cys Ala Gly Asp Thr Arg Ser Gly Gly Pro Gln Ala Asn Leu His Asp
        275                 280                 285

Ala Cys Gln Gly Asp Ser Gly Gly Pro Leu Val Cys Leu Asn Asp Gly
    290                 295                 300

Arg Met Thr Leu Val Gly Ile Ile Ser Trp Gly Leu Gly Cys Gly Gln
305                 310                 315                 320

Lys Asp Val Pro Gly Val Tyr Thr Lys Val Thr Asn Tyr Leu Asp Trp
                325                 330                 335

Ile Arg Asp Asn Met Arg Pro
            340
```

-continued

```
                        340

<210> SEQ ID NO 16
<211> LENGTH: 308
<212> TYPE: PRT
<213> ORGANISM: Artificial Sequence
<220> FEATURE:
<223> OTHER INFORMATION: Description of Artificial Sequence: part of the
      recombinant K2S molecule (modified)

<400> SEQUENCE: 16

Ser Ala Gln Ala Leu Gly Leu Gly Lys His Asn Tyr Cys Arg Asn Pro
  1               5                  10                  15

Asp Gly Asp Ala Lys Pro Trp Cys His Val Leu Lys Asn Arg Arg Leu
             20                  25                  30

Thr Trp Glu Tyr Cys Asp Val Pro Ser Cys Ser Thr Cys Gly Leu Arg
         35                  40                  45

Gln Tyr Ser Gln Pro Gln Phe Arg Ile Lys Gly Gly Leu Phe Ala Asp
     50                  55                  60

Ile Ala Ser His Pro Trp Gln Ala Ala Ile Phe Ala Lys His Arg Arg
 65                  70                  75                  80

Ser Pro Gly Glu Arg Phe Leu Cys Gly Gly Ile Leu Ile Ser Ser Cys
                 85                  90                  95

Trp Ile Leu Ser Ala Ala His Cys Phe Gln Glu Arg Phe Pro Pro His
                100                 105                 110

His Leu Thr Val Ile Leu Gly Arg Thr Tyr Arg Val Val Pro Gly Glu
            115                 120                 125

Glu Glu Gln Lys Phe Glu Val Glu Lys Tyr Ile Val His Lys Glu Phe
        130                 135                 140

Asp Asp Asp Thr Tyr Asp Asn Asp Ile Ala Leu Leu Gln Leu Lys Ser
145                 150                 155                 160

Asp Ser Ser Arg Cys Ala Gln Glu Ser Ser Val Val Arg Thr Val Cys
                165                 170                 175

Leu Pro Pro Ala Asp Leu Gln Leu Pro Asp Trp Thr Glu Cys Glu Leu
            180                 185                 190

Ser Gly Tyr Gly Lys His Glu Ala Leu Ser Pro Phe Tyr Ser Glu Arg
        195                 200                 205

Leu Lys Glu Ala His Val Arg Leu Tyr Pro Ser Ser Arg Cys Thr Ser
    210                 215                 220

Gln His Leu Leu Asn Arg Thr Val Thr Asp Asn Met Leu Cys Ala Gly
225                 230                 235                 240

Asp Thr Arg Ser Gly Gly Pro Gln Ala Asn Leu His Asp Ala Cys Gln
                245                 250                 255

Gly Asp Ser Gly Gly Pro Leu Val Cys Leu Asn Asp Gly Arg Met Thr
            260                 265                 270

Leu Val Gly Ile Ile Ser Trp Gly Leu Gly Cys Gly Gln Lys Asp Val
        275                 280                 285

Pro Gly Val Tyr Thr Lys Val Thr Asn Tyr Leu Asp Trp Ile Arg Asp
    290                 295                 300

Asn Met Arg Pro
305

<210> SEQ ID NO 17
<211> LENGTH: 268
<212> TYPE: PRT
<213> ORGANISM: Artificial Sequence
<220> FEATURE:
```

-continued

<223> OTHER INFORMATION: Description of Artificial Sequence: part of the recombinant K2S molecule (modified)

<400> SEQUENCE: 17

```
Ser Cys Ser Thr Cys Gly Leu Arg Gln Tyr Ser Gln Pro Gln Phe Arg
  1               5                  10                  15

Ile Lys Gly Gly Leu Phe Ala Asp Ile Ala Ser His Pro Trp Gln Ala
                 20                  25                  30

Ala Ile Phe Ala Lys His Arg Ser Pro Gly Glu Arg Phe Leu Cys
             35                  40                  45

Gly Gly Ile Leu Ile Ser Ser Cys Trp Ile Leu Ser Ala Ala His Cys
 50                      55                      60

Phe Gln Glu Arg Phe Pro Pro His His Leu Thr Val Ile Leu Gly Arg
 65                  70                  75                  80

Thr Tyr Arg Val Val Pro Gly Glu Glu Glu Gln Lys Phe Glu Val Glu
                     85                  90                  95

Lys Tyr Ile Val His Lys Glu Phe Asp Asp Thr Tyr Asp Asn Asp
                100                 105                 110

Ile Ala Leu Leu Gln Leu Lys Ser Asp Ser Ser Arg Cys Ala Gln Glu
            115                 120                 125

Ser Ser Val Val Arg Thr Val Cys Leu Pro Pro Ala Asp Leu Gln Leu
130                 135                 140

Pro Asp Trp Thr Glu Cys Glu Leu Ser Gly Tyr Gly Lys His Glu Ala
145                 150                 155                 160

Leu Ser Pro Phe Tyr Ser Glu Arg Leu Lys Glu Ala His Val Arg Leu
                165                 170                 175

Tyr Pro Ser Ser Arg Cys Thr Ser Gln His Leu Leu Asn Arg Thr Val
                180                 185                 190

Thr Asp Asn Met Leu Cys Ala Gly Asp Thr Arg Ser Gly Gly Pro Gln
            195                 200                 205

Ala Asn Leu His Asp Ala Cys Gln Gly Asp Ser Gly Gly Pro Leu Val
        210                 215                 220

Cys Leu Asn Asp Gly Arg Met Thr Leu Val Gly Ile Ile Ser Trp Gly
225                 230                 235                 240

Leu Gly Cys Gly Gln Lys Asp Val Pro Gly Val Tyr Thr Lys Val Thr
                245                 250                 255

Asn Tyr Leu Asp Trp Ile Arg Asp Asn Met Arg Pro
                260                 265
```

<210> SEQ ID NO 18
<211> LENGTH: 527
<212> TYPE: PRT
<213> ORGANISM: Homo sapiens (tPA)

<400> SEQUENCE: 18

```
Ser Tyr Gln Val Ile Cys Arg Asp Glu Lys Thr Gln Met Ile Tyr Gln
  1               5                  10                  15

Gln His Gln Ser Trp Leu Arg Pro Val Leu Arg Ser Asn Arg Val Glu
                 20                  25                  30

Tyr Cys Trp Cys Asn Ser Gly Arg Ala Gln Cys His Ser Val Pro Val
             35                  40                  45

Lys Ser Cys Ser Glu Pro Arg Cys Phe Asn Gly Gly Thr Cys Gln Gln
 50                      55                      60

Ala Leu Tyr Phe Ser Asp Phe Val Cys Gln Cys Pro Glu Gly Phe Ala
 65                  70                  75                  80
```

-continued

```
Gly Lys Cys Cys Glu Ile Asp Thr Arg Ala Thr Cys Tyr Glu Asp Gln
                85                  90                  95

Gly Ile Ser Tyr Arg Gly Thr Trp Ser Thr Ala Glu Ser Gly Ala Glu
            100                 105                 110

Cys Thr Asn Trp Asn Ser Ser Ala Leu Ala Gln Lys Pro Tyr Ser Gly
        115                 120                 125

Arg Arg Pro Asp Ala Ile Arg Leu Gly Leu Gly Asn His Asn Tyr Cys
    130                 135                 140

Arg Asn Pro Asp Arg Asp Ser Lys Pro Trp Cys Tyr Val Phe Lys Ala
145                 150                 155                 160

Gly Lys Tyr Ser Ser Glu Phe Cys Ser Thr Pro Ala Cys Ser Glu Gly
                165                 170                 175

Asn Ser Asp Cys Tyr Phe Gly Asn Gly Ser Ala Tyr Arg Gly Thr His
            180                 185                 190

Ser Leu Thr Glu Ser Gly Ala Ser Cys Leu Pro Trp Asn Ser Met Ile
        195                 200                 205

Leu Ile Gly Lys Val Tyr Thr Ala Gln Asn Pro Ser Ala Gln Ala Leu
    210                 215                 220

Gly Leu Gly Lys His Asn Tyr Cys Arg Asn Pro Asp Gly Asp Ala Lys
225                 230                 235                 240

Pro Trp Cys His Val Leu Lys Asn Arg Arg Leu Thr Trp Glu Tyr Cys
                245                 250                 255

Asp Val Pro Ser Cys Ser Thr Cys Gly Leu Arg Gln Tyr Ser Gln Pro
            260                 265                 270

Gln Phe Arg Ile Lys Gly Gly Leu Phe Ala Asp Ile Ala Ser His Pro
        275                 280                 285

Trp Gln Ala Ala Ile Phe Ala Lys His Arg Arg Ser Pro Gly Glu Arg
    290                 295                 300

Phe Leu Cys Gly Gly Ile Leu Ile Ser Ser Cys Trp Ile Leu Ser Ala
305                 310                 315                 320

Ala His Cys Phe Gln Glu Arg Phe Pro Pro His His Leu Thr Val Ile
                325                 330                 335

Leu Gly Arg Thr Tyr Arg Val Val Pro Gly Glu Glu Glu Gln Lys Phe
            340                 345                 350

Glu Val Glu Lys Tyr Ile Val His Lys Glu Phe Asp Asp Asp Thr Tyr
        355                 360                 365

Asp Asn Asp Ile Ala Leu Leu Gln Leu Lys Ser Asp Ser Ser Arg Cys
    370                 375                 380

Ala Gln Glu Ser Ser Val Val Arg Thr Val Cys Leu Pro Pro Ala Asp
385                 390                 395                 400

Leu Gln Leu Pro Asp Trp Thr Glu Cys Glu Leu Ser Gly Tyr Gly Lys
                405                 410                 415

His Glu Ala Leu Ser Pro Phe Tyr Ser Glu Arg Leu Lys Glu Ala His
            420                 425                 430

Val Arg Leu Tyr Pro Ser Ser Arg Cys Thr Ser Gln His Leu Leu Asn
        435                 440                 445

Arg Thr Val Thr Asp Asn Met Leu Cys Ala Gly Asp Thr Arg Ser Gly
    450                 455                 460

Gly Pro Gln Ala Asn Leu His Asp Ala Cys Gln Gly Asp Ser Gly Gly
465                 470                 475                 480

Pro Leu Val Cys Leu Asn Asp Gly Arg Met Thr Leu Val Gly Ile Ile
                485                 490                 495
```

```
Ser Trp Gly Leu Gly Cys Gly Gln Lys Asp Val Pro Gly Val Tyr Thr
            500             505             510
Lys Val Thr Asn Tyr Leu Asp Trp Ile Arg Asp Asn Met Arg Pro
        515             520             525
```